United States Patent [19]

Colbert et al.

[11] Patent Number: 5,633,363

[45] Date of Patent: May 27, 1997

[54] ROOT PREFERENTIAL PROMOTER

[75] Inventors: James T. Colbert; Bruce M. Held; Eve S. Wurtele, all of Ames, Iowa; Paul S. Dietrich, Palo Alto, Calif.

[73] Assignee: Iowa State University, Research Foundation In, Ames, Iowa

[21] Appl. No.: 253,785

[22] Filed: Jun. 3, 1994

[51] Int. Cl.$^6$ .............................. C12N 15/11; C12N 15/29; C12N 15/82; A01H 5/00

[52] U.S. Cl. ................... 536/24.1; 536/23.6; 435/172.3; 435/412; 435/320.1; 435/419; 800/205

[58] Field of Search ........................... 536/24.1, 23.6; 800/205; 435/240.4, 320.1, 172.3

[56] References Cited

U.S. PATENT DOCUMENTS 5,023,179  6/1991  Lam et al. ........................... 435/172.3

OTHER PUBLICATIONS

Held et al 1993 (Jul.) Pl. Physial. 102:1001–1008.
John et al 1992 Pl. Mol. Biol. 20 (5):821–831.
Held et al 1993 (May) Pl Physial 102 (Supplement):151 (Abstract 867).
Walden et al 1990 Eur J Biochem 192:563–576.
John et al 1991 J Cellular Biochem 15A:133 (Abstract A616).
Pedersen et al 1982 Cell 29:1015–1026.
Montoliu et al 1989 Pl. Molec. Biol. 14:1–15.
Belanger et al 1991 Genetics 129:863–872.

*Primary Examiner*—Patricia R. Moody
*Attorney, Agent, or Firm*—Lynn Marcus-Wyner

[57] ABSTRACT

The present invention is directed to promoter fragments isolated from maize and particularly to a 4.7 kbp upstream promoter region designated ZRP2 of a ZRP2 genomic DNA clone, specific fragments thereof designated ZRP2(2.0) and ZRF2(1.0) and functional equivalents thereto. The promoter has particular utility in driving root preferential expression of heterologous genes that impart increased agronomic, horticultural and/or pesticidal characteristics to a given plant. This invention is also directed to DNA molecules including said promoters and transformed plant tissue including a DNA molecule comprising a promoter of the invention operably linked to a heterologous gene or genes and the seeds thereof.

19 Claims, 14 Drawing Sheets

FIG. 1

| | | | | | |
|---|---|---|---|---|---|
| GGGCCCAAAG | GAAGGAAGTA | CTTCAGTGGA | TCAAGATGTT | GATGTTCCCT | -2523 |
| GATGGGTATG | CAGCTAACCT | GAGTAGGTGG | GGTGAACTTA | TCTACTCTGT | -2473 |
| GAGTCTTAGG | GATGAAGAGT | CATGACTTCC | ACATATGGAT | TGAACAGATT | -2423 |
| CTTCTCTGTG | CATGGACAAT | CTGGGGCGGC | ATCCAACAAC | CCTCATGGAT | -2373 |
| CGCCCGGCCA | ATCGCCGCAC | CAGTCCATCC | GCCCACCTCG | ATGAGACTTA | -2323 |
| TGTTCTTAGT | GTTGAGACTT | CAGAACTTAT | TGATAATGCT | GTATTGGATA | -2273 |
| CTTATGTTTG | TGTTCGATAC | TTATGTGAGA | ACTTGAGACT | TATGAGACTT | -2223 |
| ATGTTCTTGA | TACTTATGTT | TGTGTTGAGA | ACTTGGATAT | TTATGTTTGT | -2173 |
| GTTGGATACT | TATGTCTGTG | ATGATATATG | TGATGTATAT | ATGTGATGTA | -2121 |
| TATGTGACAT | ATGTGATGTA | TATGTGGTAT | CTTTTGTTTG | TTTGGATGGA | -2073 |
| ATAGAGAAAG | CAAATAAAAA | TGTGTATACT | GGTCACTTTG | TCGAGTGTAA | -2023 |
| CACTCGGCAA | AAAGGTGCTT | TGCCGAGTGT | TAGGGCCATA | GCACTCGGTA | -1973 |
| GAGAACCAAT | ACTTAGGCAC | CGGTAAAGCT | TTTTTGGCGA | GTGTTGTGGC | -1923 |
| CCTGGCACTC | AGCTTTGCCG | AGTGCCTCAC | AGAGCACTCG | ACAAAGAACC | -1873 |
| TGACAAATGG | ACCCGCTGGT | AAATCCTTTA | CCGAGTGCAG | GTCAGTAGAC | -1823 |
| ACTCGGCAAA | GGTAACTTCT | TTGCCCAGTG | CCGCTTAGAA | CATTTGACAA | -1773 |
| AGGGTCATCT | CCGTTACCCG | GTGTCGTGAC | GGCCGCTTTT | CTTTGCCGAG | -1723 |
| TGCCTGATAG | AAAGTACTCG | GCAAAGAAGT | CGTTGCCAAT | GTATTGTTCG | -1673 |
| CTGAGGTCTC | TTTGTCAAGT | ATTACACTCG | GCAAAGACTG | TGCCGAGTGT | -1623 |
| TTTTCAGACT | TGCCGAGTG | GTTTAAGCAC | TCAGCAAAGC | GCTCGATTTC | -1573 |
| GGTAGTGACG | GTTGTTTGGC | AATAGTAAAA | TCCAGCCCTC | TCCCGTGGGG | -1523 |
| AAAAAACTGG | TAGGATCTGG | CTCGTGGCTA | AGATTCTCTT | TCTTCCCTTT | -1473 |
| GTAAAAAAAG | AGAAGAAAAA | AAAAACGACT | GTCACGGTGC | CTTGTCTGGT | -1423 |
| AATGATCGCG | CGGTCGGCTC | TGTCCTAACC | CGTAAGATGG | ACGGGAGCTG | -1373 |
| ATGATAGCGT | GACCTCCAAA | TAAACAACAA | GGGCGTGTTC | CCCGCGGTCG | -1323 |
| AATATTTTAA | GGGCCACTGA | TTAGGTGCGG | TTGAATACAT | CAACTTCACG | -1273 |
| AACATCATCT | GATCTGATCT | GATTTGGTCT | GATATGATCT | GGGTAGTCAT | -1223 |
| TTCTGCAATG | AGCATCTATC | AGGTGAACCA | ATTAATATTG | ATGACATTAT | -1173 |
| GAGTTCGAAG | ATATACTCTA | AAGTGTTATC | TAAATACAGA | AGACATTCGT | -1123 |
| TCGTTCTTTG | CCTATAACTC | TAAAAGGCTT | GTAACACCCT | CATTCATCCT | -1073 |

FIG. 1A

```
CTATATACGA  AGACTCTCTC  CTATCATTTT  TATCGATTTA  TTTTTTTTAT  -1023
ATTTAGACAA  TGGAATTAAA  TAGAACTAAA  ATATATATAA  GATGATATCT  - 973
GAGGACCCGA  GATGGTAATG  GGGACTCGAT  CCTCGATTCT  CCACGGAGAA  - 923
TTCCTCTAGG  ATATAGGTAA  TTTGTCCCCA  CGAGGATTGA  AACGGGGTAA  - 873
TTTGGTCCCC  ATGTGCCCGT  CCCGCGAACT  TCTCTTGATC  TAAATTAGTC  - 823
TATTTCCATG  TTAAAACTAT  ACTAAAAATT  TAATACACAG  TCTATTATAA  - 773
AATAGCAAAC  TAAATTCTAA  AGTTGATGCA  TCTTGTAATT  TTAAATCTGG  - 723
TTTGTTCAAG  TTATATTCAT  TTGATATAAT  AAATTTGAAT  TTGACTCTTA  - 673
ATATCGTATT  TTTTCCTAAC  GGGGACGGAT  TCTCCACGGG  GATAAATTCC  - 623
ATGATACAGA  TGGGATGAAA  GAAAAATCTC  CCGTATGAAC  TTTTGCAGGA  - 573
ATGGGGATGG  GCCAGAGAAA  TTTTCTCCCT  GCGGGACGG   GGGAGCCATA  - 523
TCCTCGGTGG  AGAATTTCCC  ATTATCATCC  TTATTTGTGG  TACATATATA  - 473
TGCATAATCT  TTTTTTTTTG  ACTGACATGT  GGGAAAGTAT  CCCATATCAA  - 423
TAGTAGAAAA  TCTTGGGAAC  GGTAGGATCG  AACACAAAGA  TCAGCTAGCT  - 373
TGTAATCACC  GAGCCATATA  GCTAGAGGGT  AATAGATCAT  GAATCAAATG  - 323
TTTTTTTCAT  AAATTATTAA  GGCTCTAAAT  TATTTTTAAT  TTAAAAATAA  - 273
ATAAAAATAT  AGTTCGATTC  TTACATTTTA  TAGTGTAAAA  CTTTAAAGTC  - 223
TATTATTACC  CCTACTTATT  GAGTTATGGT  TCAGTTCTTG  TCGACGGAGA  - 173
GTAATGAGAT  ATAGAATAAG  GTACCCTATA  GAATAAAGAA  TCTTTCTCTG  - 123
AAAAGTCTGA  CGTACGTAAA  TAAGATATAA  TAAAAAAAAT  ACAAAGAGAA  -  73
GCGCTGGACT  GGAGATGCTC  CTATATGCGG  CAATGCCTGT  GCTTATAAAT  -  23
AGCCACCTCG  GTCGGCAAGG  ACATGAACGG  CGGACGCAGT  GTGCATGCAT     28
                                  +1
ACAAGAGCAA  CAAGATACTG  GCGCAGAGGA  GCA ATG                   64
```

FIG. 1B

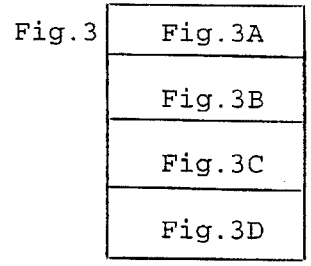

```
                                                                             56
CGCAGTGTGC ATGCATACAA GAGCAACAAG ATACTGGCCG CAGAGGAGCA ATG CCC
                                                       Met Pro
                                                        1
GGC CGT GCG GCA GCT GCC CAT CCT CCG GCG GCG GCT GCG GAC GAC ATG    104
Gly Met Asp Ala Phe Ala Ala Val Ser Leu Leu Ala Thr Leu Phe Leu
         5                  10                  15
GTT CGT GCG GCA GCT GCC CAT CCT CCG GCG GCG GCT GCG GAC GAC ATG    152
Val Arg Ala Ala Ala Ala His Pro Pro Ala Ala Ala Ala Asp Asp Met
        20                  25                  30
ACG CCG ACG GAC TAT TGG CGA GCG GTG CTT CCT GAG ACC CCG ATG CCC    200
Thr Pro Thr Asp Tyr Trp Arg Ala Val Leu Pro Glu Thr Pro Met Pro
35                  40                  45                  50
CGA GCC ATA CTC GAC CTA TTG ACC ACA TCT ACA GGT GAG GAA GGC TCA    248
Arg Ala Ile Leu Asp Leu Leu Thr Thr Ser Thr Gly Glu Glu Gly Ser
                    55                  60                  65
AGG AAG GTC ACC ACG TCA AAT GGG TAC CAA GGC CAT GAC TTA AGG ACG    296
Arg Lys Val Thr Thr Ser Asn Gly Tyr Gln Gly His Asp Leu Arg Thr
            70                  75                  80
GTC AGC ACA TCA TAT GCA TCT CAA GAT GGG GAC AAC TCA TGG AAG GCC    344
Val Ser Thr Ser Tyr Ala Ser Gln Asp Gly Asp Asn Ser Trp Lys Ala
        85                  90                  95
ACC ATG TCA TAT GGG TTC CAA AGT GGT GAG GGC TCG AGG AAG GTC ACC    392
Thr Met Ser Tyr Gly Phe Gln Ser Gly Glu Gly Ser Arg Lys Val Thr
    100                 105                 110
ACA TCA TAT CCG TAC CGA GGC CAG GAC TTA AGG ATG GTC AGC ACA TCA    440
Thr Ser Tyr Pro Tyr Arg Gly Gln Asp Leu Arg Met Val Ser Thr Ser
115                 120                 125                 130
TAT GTA TCT CAA GAT GAG GAC AAG TCA TGG AAG GTC TCG ATG CCA TCT    488
Tyr Val Ser Gln Asp Glu Asp Lys Ser Trp Lys Val Ser Met Pro Ser
                135                 140                 145
AGG TCC CAA GTT GGT GAG GGC TTA AGG AAG CTC ACC ACA CCA TTC GAA    536
Arg Ser Gln Val Gly Glu Gly Leu Arg Lys Leu Thr Thr Pro Phe Glu
            150                 155                 160
```

FIG. 3A

```
TCA CAA AGG AAG GAC TCA AGG AAG GCC ACC GCA TCA TAT GGA ATC CAA    584
Ser Gln Arg Lys Asp Ser Arg Lys Ala Thr Ala Ser Tyr Gly Ile Gln
        165                 170                 175
GAT GAT GAG GAC ACA AGG AAG GCC ACT ACA TCA TAT GGA ATC CAT GGG    632
Asp Asp Glu Asp Thr Arg Lys Ala Thr Thr Ser Tyr Gly Ile His Gly
    180                 185                 190
GAG GAC CCA AGA AAG GCC ACC ACG TCA TAT GGT TCC CAG GAT GAG AAG    680
Glu Asp Pro Arg Lys Ala Thr Thr Ser Tyr Gly Ser Gln Asp Glu Lys
195                 200                 205                 210
GGA TCA AGG AAG GTC ATA ATG TCA TAT GGG TCT AAT GGT GAG GAT GAT    728
Gly Ser Arg Lys Val Ile Met Ser Tyr Gly Ser Asn Gly Glu Asp Asp
            215                 220                 225
CCA AGA AAG GCC ACC ACA TCA TAT GGA ATA CAA GAT AAA GAG TAT CCC    776
Pro Arg Lys Ala Thr Thr Ser Tyr Gly Ile Gln Asp Lys Glu Tyr Pro
                230                 235                 240
AGG AAG GCC ACC ACA TCT TAT GGA GTT CAA GGT GAG AAG GAC CCA AGG    824
Arg Lys Ala Thr Thr Ser Tyr Gly Val Gln Gly Glu Lys Asp Pro Arg
            245                 250                 255
GAA GCT ACC ATC TCA TAT GGG TCC CAG GAT GAT GAG GAT TCTC AGA AAA   872
Glu Ala Thr Ile Ser Tyr Gly Ser Gln Asp Asp Glu Asp Ser Arg Lys
        260                 265                 270
GTC AAC ATG TCA TAT GGG TCT AAT GGT GAG GAC GAC CCA AGA AAG GCC    920
Val Asn Met Ser Tyr Gly Ser Asn Gly Glu Asp Asp Pro Arg Lys Ala
275                 280                 285                 290
ACC ACA TCA TAT GGG TCC CAT GGT GAG TAT GAA TCA AAT AAG GCC ACA    968
Thr Thr Ser Tyr Gly Ser His Gly Glu Tyr Glu Ser Asn Lys Ala Thr
                295                 300                 305
ATG TCA TAT GGG TTC CAA GGC ATG GAA GAT TTA AGG AAG GCC ACC ACA   1016
Met Ser Tyr Gly Phe Gln Gly Met Glu Asp Leu Arg Lys Ala Thr Thr
            310                 315                 320
TCA TAT GGA ATA CAA GAT GAA GAG TAT CCA AGG AAG GCC ACC ACA TCA   1064
Ser Tyr Gly Ile Gln Asp Glu Glu Tyr Pro Arg Lys Ala Thr Thr Ser
        325                 330                 335
TAT GGA GTT CAA GGT GAG GAG GAC CCA AAG AAA GAT ACC ATG TCA TAT   1112
Tyr Gly Val Gln Gly Glu Glu Asp Pro Lys Lys Asp Thr Met Ser Tyr
    340                 345                 350
GGG TCA CAA GAT GAC GAG GAA TCT AGA AAA ATC AGC ATC TCA TAT GGG   1160
Gly Ser Gln Asp Asp Glu Glu Ser Arg Lys Ile Ser Ile Ser Tyr Gly
355                 360                 365                 370
TCT AAT GGT GAG AAC GAC TCA AGA ACG TCC ACC ACA TCA TAT GGG TCC   1208
Ser Asn Gly Glu Asn Asp Ser Arg Thr Ser Thr Thr Ser Tyr Gly Ser
            375                 380                 385
CAA GGT AAG GAG ATC CTA AGA AAG GTC ACC ACG TCA TGT GAT AGG TAC   1256
Gln Gly Lys Glu Ile Leu Arg Lys Val Thr Thr Ser Cys Asp Arg Tyr
        390                 395                 400
```

FIG 3B

```
CAC AGT TGT GAA GAT GAT GCG CGG AAG GCC ACC GCA TCA CAT AGA GCT    1304
His Ser Cys Glu Asp Asp Ala Arg Lys Ala Thr Ala Ser His Arg Ala
        405                 410                 415
GAA GGT AAG CAG GAC ATG AAG AAG ATC AGC ATA TCA TAT GGA TCT CAT    1352
Glu Gly Lys Gln Asp Met Lys Lys Ile ser Ile Ser Tyr Gly Ser His
    420                 425                 430
CGA AGT GGG GAG CAC TCA TTG AGA ACC ACC AGT ACA AGA GAG AAA GGT    1400
Arg Ser Gly Glu His Ser Leu Arg Thr Thr Ser Thr Arg Glu Lys Gly
435                 440                 445                 450
GAC ACA AGT AAA GGG GAC ATC CAT CAC CAT GAC CAT GCT GCC GTT CAC    1448
Asp Thr Ser Lys Gly Asp Ile His His His Asp His Ala Ala Val His
                455                 460                 465
ATC CAC AGC AGC GGC AAC AAG CTA GTA GCA GAT GTT TTC TTC TTC CAC    1496
Ile His Ser Ser Gly Asn Lys Leu Val Ala Asp Val Phe Phe Phe His
            470                 475                 480
GAC GTC CCT ACG ACC AGG GTC CGT AAT CAC GCC GAT CAT CCC ACC GAC    1544
Asp Val Pro Thr Thr Arg Val Arg Asn His Ala Asp His Pro Thr Asp
            485                 490                 495
CAC CAC CCT ACC ACC TCT GCT GCC TCT CCG CGA GGC CGA CGC GCT CCC    1592
His His Pro Thr Thr Ser Ala Ala Ser Pro Arg Gly Arg Arg Ala Pro
        500                 505                 510
GTT CTC CAC CGG GCG CTT CGC CGA CAT CCT CGC CAT GTT CGC GCC GAC    1640
Val Leu His Arg Ala Leu Arg Arg His Pro Arg His Val Arg Ala Asp
515                 520                 525                 530
GAC ATC CGA CGC CAT GGG CGA AGA GAT ACG GTC GAC GCT CGA CAC CTG    1688
Asp Ile Arg Arg His Gly Arg Arg Asp Thr Val Asp Ala Arg His Leu
                535                 540                 545
CGA GAA CAC GCG CCC GCT CCC CGG CGA GAA GGC CGA CTG CGA CAC CTC    1736
Arg Glu His Ala Pro Ala Pro Arg Arg Glu Gly Arg Leu Arg His Leu
            550                 555                 560
CCT CGA GTC TCT CGC CAG GAT ACC CGC CGT CCT CCT CGG GAC ACG CAA    1784
Pro Arg Val Ser Arg Gln Asp Thr Arg Arg Pro Pro Arg Asp Thr Gln
        565                 570                 575
CGT CCG CGC TTT CTC CGG CGA CAT GCC CAC CGA TCC TGC CGG CAC GTA    1832
Arg Pro Arg Phe Leu Arg Arg His Ala His Arg Ser Cys Arg His Val
    580                 585                 590
GGC GAA GGG GGG GCG GTA TAACGTAACG GCCGTGCACA AGCTCTCCGA           1880
Gly Glu Gly Gly Ala Val
595                 600

GTCACTGACG GCGGCGGCGT GCCATGACCT GACGTACCAC TACGACGTGT TCTACTGCCA  1940
```

FIG.3C

```
CACGACCAAC CCGGCGGCCA CGTACCTGGT GAAGCTGGCA GCCCAGGATG GCGGGGCGGC 2000

GGACATGGAG GCGTTGGTCG TGTGCCACCT CGACACGTCG TTGTGGAGTC CCAGACACCC 2060

ATTTTTGGTG GCGCACAGTC TCAAGCCAGG GGACGACGCA GTCGTGTGTC ATTTTCTCTC 2120

TAAGCTCAGC ATCGTCTGGG TCCCCGCTGG CGAGCAGGGG TGGCGTGCGT GAAGTGAAGC 2180

CCAATTAGCG TTAAGTACCC GTGCTCAGAG CTCTATCTGT AACCTGTGTG GACCTAACGT 2240

GGCTCTGTAA TGCTAAATAA AAACCTGCGT CAATCATGTA TCGTGATATT TTATCTGTTT 2300

TAGCAAAAA AAAAAAAAAA AAAAAAAA                                    2329
```

FIG. 3D

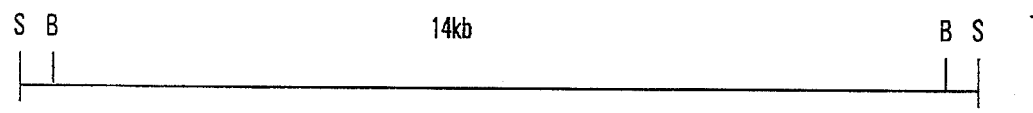
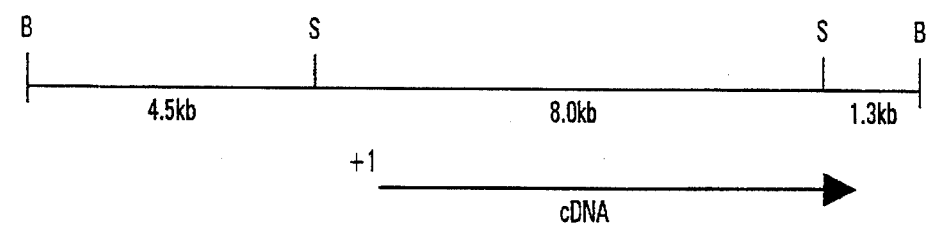
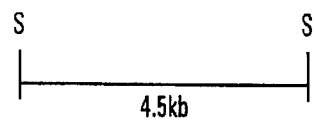
FIG.4

```
            H
            i
            n                       E               B
            d    X    N    S    c    S    P    a
            I    b    S    a    o    p    s    m
            I    a    I    l    R    h    t    H
            I    I    I    I    V    I    I    I

5'    AGCTTCTAGATGCATGTCGACGATATCGCATGCTGCAGG    3'
      |||||||||||||||||||||||||||||||||||||||
3'    AGATCTACGTACAGCTGCTATAGCGTACGACGTCCCTAG           5'
```

FIG. 5

ROOT PREFERENTIAL PROMOTER

BACKGROUND OF THE INVENTION

The selection of a promoter in the genetic engineering of a heterologous gene is often a critical factor in obtaining expression of the desired gene. It is the nucleotide sequence of the promoter at the 5' end of a structural gene which is either directly or indirectly recognized and bound by a DNA-dependent RNA polymerase during the initiation of transcription of the gene. It is generally recognized by those skilled in the art, that the localization of gene expression is desirable in a tissue-specific manner.

Expression of tissue-specific plant genes has been identified genetically and by their differential expression in various organs, for example: embryo-specific gene expression of seed storage proteins including, glycinin, legumins, zeins, and glutenin; fruit ripening gene expression including polygalacturonase; and differential expression of root nodulation genes in leguminous plants including nodulin. It would be desirable to regulate tissue specific heterologous gene expression with a promoter which was preferential to the specific tissue where expression was required. The ability to control levels of gene expression is very important and expression of the protein product may impart increased agronomic, horticultural and/or pesticidal characteristics to a given crop plant.

SUMMARY OF THE INVENTION

This invention relates to a root preferential promoter isolatable from maize (Zea mays). The promoter may be operably linked to any desired heterologous gene and will preferentially direct the expression of that gene in root tissue. A specific promoter element of the invention has been designated ZRP2 and specific fragments thereof are designated ZRP2(2.0) and ZRP2(1.0) since they were obtained from a ZRP2 genomic clone of maize. The transcribed region of this ZRP2 gene exhibited strong hybridization to a mRNA species abundant in roots. Therefore in a first aspect, the present invention is directed to a promoter region designated "ZRP2" which is characterized by about a 4.7 kbp region upstream of the putative translation start site of the genomic ZRP2 done and wherein said promoter controls the preferential expression of a downstream heterologous gene. Additionally, promoter fragments of ZRP2 are claimed which correspond to about a 2.6 kbp fragment, FIG. 1, (SEQ ID No: 1); a 2.0 kbp fragment designated ZRP2(2.0) and located immediately upstream of the translation start point, ATG (base pairs 62–64) of FIG. 1 (SEQ ID No. 1, base pairs 2634–2636); and about a 1.0 kbp fragment designated ZRP2(1.0) located immediately upstream of the translation start point as depicted in FIG. 1 (SEQ ID No: 1) and functionally equivalent nucleotide sequences thereto and parts thereof.

In another embodiment, the present invention also includes a recombinant DNA molecule comprising a promoter of the invention and a plant expressible nucleotide sequence, wherein the sequence is placed under the regulatory control of transcription initiating and activating elements of the promoter. In particular, the promoter can be combined with a variety of DNA sequences, typically heterologous genes, to provide recombinant DNA molecules for regulated transcription and translation of said DNA sequences and which allow for regulated control of expression. In a further embodiment, the present invention is directed to a recombinant vector, preferably a plasmid, comprising the recombinant DNA molecules described above.

Such recombinant DNA molecules or vectors including the DNA molecules, may be introduced into plant tissue so that the promoter preferentially directs the expression of the heterologous gene to roots. It is contemplated that the present invention is generally applicable to the expression of heterologous genes in monocotyledonous and dicotyledonous plants, particularly monocotyledonous plants.

The present invention also encompasses a method for conferring decreased susceptibly to vital, fungal and insect diseases causing plant root damage comprising inserting into a vector a promoter of the invention and inserting into said vector a heterologous gene or part thereof that encodes for a protein or peptide that confers decreased susceptibility to vital, fungal or insect damage such that said heterologous gene is downstream from said promoter and so orientated relative to said promoter to be under expressible control thereof; and transforming a plant or plant tissue with said vector, wherein the roots of said transformed plant or plant tissue express the protein or the peptide that confers decreased susceptibility to said damage. The invention is further directed to transformed plants or plant tissue which include the recombinant DNA molecules of the invention and seeds and plants produced from the transformed plants or plant tissue thereof.

BRIEF DESCRIPTION OF THE FIGURES

FIG. 1 describes a fragment of the nucleotide sequence of the ZRP2 promoter region of the genomic ZRP2 DNA clone. This fragment is about 2633 base pairs and corresponds to SEQ. ID. No:1. The approximate transcription start point is designated +1 and the putative translation start ATG is bolded. The TATA box is a 7 base pair sequence "TATAAAT" located from base pair −29 to −23. In this specification the nucleotides are numbered in negative order from the transcription start point (ATG) with −1=bp 2572 of SEQ ID No:1. The leader sequence corresponds to nucleotides 1 through 61 (bp 2573 to 2633 of SEQ ID NO:1)

FIG. 3 describes the nucleotide sequence and predicted amino acid sequence of the ZRP2 cDNA clone and corresponds to SEQ. ID. No: 2 and SEQ ID No: 3.

FIG. 4 describes partial restriction enzyme maps of the ZRP2 genomic clone. A) ZRP2 genomic clone in lambda, B) pZ2B, the entire genomic clone, C) pZ2.45SS and D) pZ2.1ES. The restriction enzymes are (S) Sal I, (B) Barn HI, (E) Eco RV, and (Sp) SphI. The relative position of the pZRP2 cDNA to the ZRP2 genomic clone is shown in panel B.

FIG. 5 describes the custom polylinker cloned into pGem-3Z and corresponds to SEQ ID Nos: 4 and 5.

DETAILED DESCRIPTION OF THE INVENTION

Figure 2:
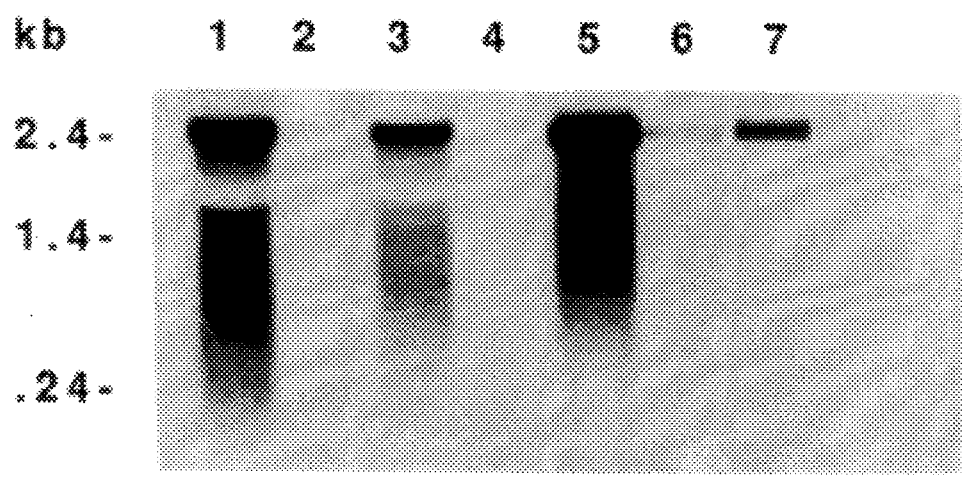
FIG. 2 describes total RNA (10.0 µg) from three-day-old roots (lane 1), five-day-old leaves (lane 2), three week old roots (lane 3), and leaves (lane 4) one haft of a microgram of poly (A)+ RNA from nine-day-old roots (lane 5) light grown nine day old shoots (lane 6) and etiolated nine-day old shoots (lane 7).

As used throughout the specification the following definitions apply:

Expression refers to the transcription and/or translation of a heterologous gene in plant tissue. Expression will preferentially be directed to plant root tissue.

Heterologous gene refers to a DNA sequence encoding any peptide or protein or portion thereof other than the ZRP2 polypeptide. The heterologous gene may be derived in whole or part from any source known in the art, and may contain one or more modifications in either the coding or untranslated regions which could affect the biological activity or the chemical structure of the expression product.

Promoter refers to that portion of the DNA upstream from the coding region, that contains the binding site for RNA polymerase II and initiates transcription of the DNA. The promoter region also includes other elements that act as regulators of gene expression. Other regulatory elements which may be present are upstream activators, enhancers, and/or repressors.

A functionally equivalent sequence refers to a DNA sequence which has promoter activity substantially similar to ZRP2 (the approximate 4.7 kbp upstream region of the translation start site of the genomic clone); ZRP2(2.0); ZRP2(1.0) or parts thereof and is complementary to a DNA sequence which under stringent hybridizing conditions will hybridize with the said promotor sequences. Stringent conditions are those in which hybridization is effective at 60° C. in 2.5× saline citrate buffer followed by mere rinsing at 37° C. at a reduced buffer concentration which will not affect hybridization that took place. It is understood in the art that nucleotide sequence mismatches can occur without causing changes in the function of the DNA sequence. Homology of specific DNA sequences may be identified by those skilled in the art using stringent hybridization conditions. Extent of homology is often measure in terms of percent of identity between the compared sequences. In this specification, it will be understood that functionally equivalent sequences will have at least 75% sequence homology. This means at least 75% of the nucleotides in the compared sequences will be identical. Preferably homology will be at least 85%.

This invention includes parts of promoter fragments and their functional equivalents. A part of a promoter fragment refers to a nucleotide sequence which functions substantially similar to the ZRP2 promoter, the ZRP2(2.0) fragment, the ZRP2(1.0) fragment and having at least 100 adjacent nucleotides of the sequence depicted in SEQ ID No.:1 or a functional equivalent thereto. More preferably the part has at least 50 such nucleotides, and still more preferably the part has at least 10 such nucleotides. It is recognized, that regions smaller than the 1.0 kbp ZRP2 promoter fragment, (ZRP2 (1.0)) as defined herein could be sufficient to confer preferential root expression. This can be tested by making deletions in the promoter and then assaying for retention of activity. Such assays are within the skill of the ordinary artisan.

Plant tissue refers to differentiated and undifferentiated tissues of plants including but not limited to roots, shoots, leaves, pollen, seeds, tumor tissue, and cells in culture including callus tissue, single cells, protoplasts, and embryos.

The isolation and characterization of a promoter which is active in plants to control and regulate the expression of a downstream heterologous gene is described in the present work. The primary objective of this invention is to provide recombinant DNA molecules comprising a promoter region which will enable those skilled in the art to preferentially express heterologous genes in plant root tissue. The promoter comprises the DNA sequences from the 5' nontranslated regions of ZRP2 genes that initiate and regulate transcription of genes place under its control. The DNA sequence is found as a naturally occurring region upstream of the plant ZRP2 gene and is isolated from a maize genomic library. Therefore, in a preferred embodiment, the promoter sequence is derived from the 4.7 kbp upstream region starting at the putative translation site (base pair 61 of FIG. 1) of the plant ZRP2 gene from maize.

The sequence of promoter fragments ZRP2(2.0) and ZRP2(1.0) is given in FIG. 1. (SEQ. ID. No: 1). ZRP2(2.0) corresponds to the 2.0 kbp fragment of ZRP2 genomic DNA upstream of the putative translation start site, ATG starting at bp 61 of FIG. 1. ZRP2(1.0) corresponds to the 1.0 kbp fragment of upstream ZRP2 genomic DNA described in FIG. 1, SEQ ID No:1. FIG. 1, SEQ ID No: 1, also describes the upstream sequence of an additional 633 base pairs of the ZRP2, 4.7 kbp promoter region, and the entire sequence is designated ZRP2 (2.6).

Figure 8:
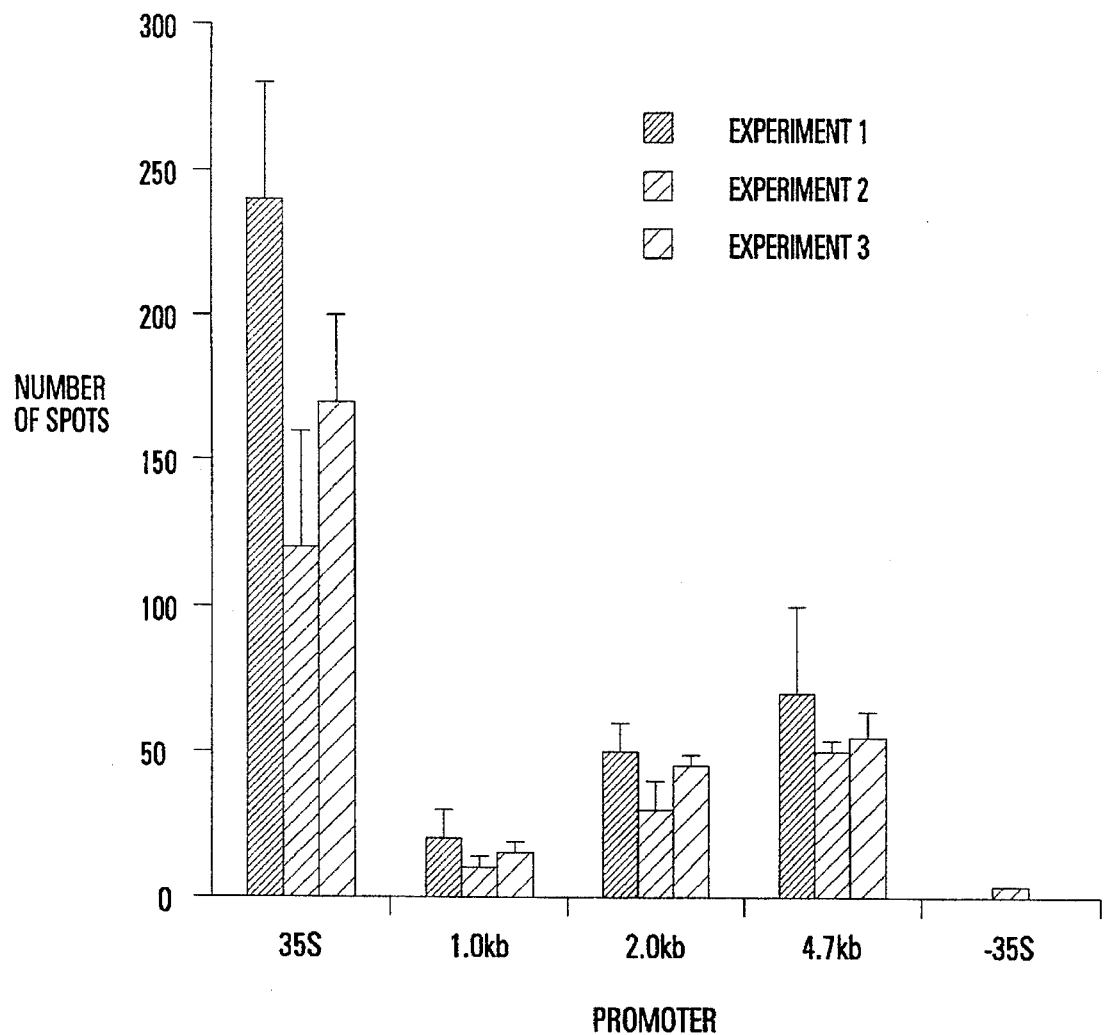
FIG. 8 describes the promoter activity in maize roots of the ZRP2 and 35S GUS/Fusion constructs of FIG. 7.

The function of the ZRP2 polypeptide is unknown. Analysis of the activity of the different ZRP2 promoter fragments in maize reveals that the 1.0 kbp of upstream sequence is enough to direct transcription of a reporter gene to the root. However, additional upstream sequences increase the strength of the promoter in the root. (FIG. 8). Without being held to a specific hypothesis, it is speculated that the 1.0 kbp upstream region, ZRP2(1.0) confers organ specificity and that other sequences further upstream act as long range enhancer elements. Therefore, a recombinant DNA molecule of the invention may contain in addition to the ZRP2 promoter region and fragments of the invention other cis-element(s) which would confer ZRP2 root preferential transcription, and particularly including other ZRP2 DNA promoter fragments including at least 100 adjacent nucleotides, preferably 50 such nucleotides and more preferably 10 such nucleotides.

It is also contemplated by the invention that one or more intron sequences in the downstream region of the ZRP2 genomic clone may contribute to increased promoter activity of the said ZRP2 fragments or parts thereof.

Therefore specific embodiments of the invention include:

a) a ZRP2 promoter, a 4.7 kbp sequence immediately upstream of the putative translation start point (ATG) of the ZRP2(2.6) sequence exhibited in FIG. 1, SEQ ID No.: 1;

b) a promoter nucleotide sequence designated ZRP2(2.6) upstream of the putative translation start point (ATG) depicted in FIG. 1, SEQ ID No: 1;

c) a ZRP2(2.0) promoter fragment located upstream of the putative translation start point starting at base pair 61 of FIG. 1, SEQ ID No: 1;

d) a ZRP2(1.0) promoter fragment located upstream of the putative translation start point starting at base pair 61 of FIG. 1, SEQ ID No: 1;

e) functionally equivalent sequences of a), b), c) and d);

f) parts of a) through e); and g) composite ZRP2 promoter fragments wherein said composite fragment includes a promoter as defined in a) through f) above and other cis-elements or trans-elements.

An example of a composite ZRP2 promoter includes the ZRP2(1.0) fragment of SEQ ID No: 1 and at least 10 adjacent base pairs of an upstream sequence to ZRP2(1.0) of SEQ ID No: 1. A further example of a composite ZRP2 promoter includes the ZRP2(1.0) fragment of SEQ ID No: 1 and at least 10 adjacent base pairs of one or more intron sequences located in the ZRP2 genomic gene.

Another aspect of the invention is conferring activity on an otherwise inactive but inducible or regulatable promoter by operably linking to or inserting within an inducible or regulatable promoter one or more promoter sequences of the invention which alone or combined give preferential root expression.

The invention further includes DNA molecules comprising said promoters operably linked to one or more heterologous genes. The promoters of the invention may be used to express any heterologous gene desired. Examples of suitable genes and their associated phenotype include but are not limited to: insect resistance conferred by an insecticidal toxin or other protein, such as crystal encoding toxin genes of Bacillus thuringiensis; herbicide resistance conferred by various herbicide resistance mechanisms; viral coat protein and/or RNA, or other viral or plant genes to confer viral resistance; fungus resistance; antisense RNA to confer virus resistance or to modify expression of an exogenous or endogenous gene of the host plant; yield improvement; drought resistance; improved nutritional balance coffered by an organ storage protein gene; nitrate tolerance; plant morphology; metabolic alternations that increase or modify production of useful plant products such as sugars, starches, oils and the like. Other sons of useful heterologous genes in plants will be recognized by one skilled in the art.

In some instances, one or more heterologous genes may be introduced in a single recombinant DNA molecule or vector, in order to provide an easily measured phenotype linked to a difficultly measurable phenotype. An example is kanamycin resistance linked to a gene for fungal resistance.

A recombinant DNA molecule of the invention may also include other sequences, for example intron sequences, such as intron 6 from alcohol dehydrogenase; 3' untranslated sequences, such as the proteinase inhibitor II 3' untranslated region; and termination sequences at the end of a transcriptional unit that signals termination of transcription, such as the nopaline synthase terminator.

Transformation can be carried out by any means known in the art. These include, but are not limited to, direct transfer of DNA into whole cells, tissues or protoplasts, optimally assisted by chemical or physical agents to increase cell permeability to DNA, for example treatment with polyethylene glycol, dextran surfate, electroporation, and ballistic implantation. Transformation can also be mediated by Agrobacterium strains and by variously genetically engineered transformed plasmids which include portions of the T-DNA of the tumor-inducing plasmids of Agrobacterium. Other means for affecting entry of DNA into cells include viral vectors (transfection and transduction) and agroinfection.

Construction of transformation vectors incorporating a DNA molecule of the invention is readily accomplished by standard techniques of DNA manipulation. Examples of vectors suitable for plant transformation include, but are not limited to plasmids. Transformed cells, protoplasts or plant tissue are cultured in an appropriate culture medium and a transformed plant is regenerated.

Virtually all plants of agronomic or horticultural value are known to be transformable and regenerable. The techniques vary in individual detail depending on the species to be transformed as is understood by those skilled in the art. In general, both monocotyledonous and dicotyledonous plants are suitable for use in the invention. Specific mention is made of corn (maize) sweet corn, soybean, sugar beet, sunflower, tomato, pepper, cabbage, broccoli, onion, wheat, barley, oats and rice. Particularly corn and sweet corn.

The following examples are given by way of illustration and are not intended to limit the invention in any manner.

EXAMPLES

Many of the examples disclose techniques that are standard and well known in the art. Rather than disclose these in detail references have been cited. The references cited herein are incorporated by reference. In general, methods for cloning and preparing plasmid DNA are essentially as described (Sambrook et at. (1989) Molecular Cloning, 2nd ed., Cold Spring Harbor Laboratory.

Example 1

RNA Isolation

A variety of maize (*Zea Mays* NKH31) organs are analyzed to determine ZRP2 mRNA accumulation by gel blot analysis (B. Held (1993) Dissertation: Root-preferential mRNA accumulation in Zea mays. Iowa State University). Comparison of ZRP2 mRNA accumulation between the root and leaf organs at different developmental stages confirm root-preferential accumulation of ZRP2 mRNA (FIG. 2).

RNA gel blot analyses and hybridization conditions are performed as described (Cotton et al, (1990) Plant Molec. Biol.14:707–714). RNA size standards are from Bethesda Research Laboratories. The full length ZRP2 cDNA in pBluescript (SK) is digested with HindIII and transcribed with T3RNA polymerase (Promega) to produce a $^{32}$P-labeled RNA probe. The full length ZRP2 cDNA, FIG. 3, SEQ ID No.:2 is described (I. John (1991) Dissertation: Isolation and characterization of two root-preferential cDNA clones from Zea mays (Colorado State University). It is 2304 bp in length excluding the poly(A) tail. A putative polyadenylation signal sequence occurs 43 nucleotides upstream of the poly(A) tail.

Example 2

Subgenomic construction and screening

Genomic DNA is isolated from maize leaves (Saghai-Maroof et al. (1984) Proc. Natl. Acad. Sci. 81:8014–8018), digested to completion with Bam HI, and fractionated on a 1% agarose gel. DNA fragments (10–21 kbp) are isolated by electo-elution, ligated into Lambda Dash II digested arms, and packaged into GigapackII Packaging Extracts (Stratagene). The subgenomic library of about 100,000 plaques is screened with a $^{32}$P-labeled ZRP2 cDNA according to standard procedures (Davies et at., (1980) Advanced Bacterial Genetics, Cold Spring Harbor, N.Y. Cold Spring Laboratory). One hybridizing clone is detected which also hybridized to the ZRP2 cDNA probe. Subsequent screenings indicate that the genomic done corresponds to the ZRP2 cDNA clone. (SEQ ID No.:2). Partial sequencing of the subclone from primer 501 reveals sequence identity to the sequence found at the 5' end of the ZRP2 cDNA sequence.

Restriction mapping of the genomic clone reveals an insert 14 kbp in size. (FIG. 4). The insert contains two internal Sal I restriction sites which divide the cloned insert into about 4.5. 8.0 and 1.3 kbp fragments. The 8.0 kbp fragment hybridized to the 5' end of the ZRP2 cDNA, and the 1.3 kbp fragment hybridized to the 3' end of the ZRP2 cDNA. Therefore the ZRP2 gene appears to be approximately 9.0 kbp in length. The ZRP2 cDNA is about 2.3 kbp (FIG. 3, SEQ ID No:2). It is postulated that intron sequences make up the remaining 7.0 kbp of genomic sequence. It is also contemplated that one or more of these intron sequences may contribute to promoter activity.

Example 3

DNA Sequencing

The ZRP2 promoter fragments are sequenced at the Iowa State University Nucleic Add Facility, according to the dideoxy-nucleotide chain termination method with double stranded DNA templates (Chen and Seeburg, (1985) DNA 4: 165–170) and depicted in FIG. 1 corresponding to SEQ ID No: 1. Subclones pZ2B in pBluescript (KS) corresponding to the entire genomic ZRP2 fragment; pZ2.45SS in pBluescript (KS); and pZ2.1ES in pBluescript(KS), corresponding to the ZRP2(1.0) fragment provide the templates for sequencing. After screening of the subgenomic library, Lambda DNA is isolated from the genomic clone, digested with BamHI, and the BamHI fragment is cloned into BamHI digested pBluescript (KS) to form pZ2B. The plasmid pZ2.45SS is constructed by digesting out a 4.5 kbp SaI fragment from the Lambda genomic done and ligating it into SaII digested pBluescript(KS). The plasmid pZ2.1ES in pBluescript (KS) is constructed by digesting pZ2B with EcoRV and SphI, which liberates the 1.0 kbp promoter fragment. This fragment is cloned into the EcoRV and SphI sites of pGem 1.0 resulting in pZ2.1ES in pGem 10. The plasmid pGem 10 is constructed by cloning a custom polylinker into the BamHI and HindIII sites of pGem-3Z (FIG. 5, SEQ ID NO: 4 and 5). The sequence of the 5' end of the polylinker is depicted in SEQ ID NO:4). The HindIII/BamHI fragment containing the 1.0 kbp promoter fragment is then cloned into the HindIII and BamHI sites of pBluescript(KS) to form pZ2.1ES in pBluescript (KS). The M13 reverse primer was used to sequence pZ2.45SS in pBluescript (KS) and pZ2.1ES in pBluescript(KS). Synthesized oligonucleotides are used as primers to sequence in both directions the pZ2B clone.

The sequence of primer 501 5' CACAGCAGCGAAG-GCATC 3', SEQ ID NO.:6, was at the 5' end of the ZRP2 cDNA sequence.

The remaining primers:

| 2.3 | 5' AAATAAGGATGATAATGG | 3', SEQ ID NO.: 7; |
| 2.4 | 5' AGTTATATTCATTTGATA | 3', SEQ ID NO.: 8; |
| 2.5 | 5' CCGAGCCATATAGCTAGA | 3', SEQ ID NO.: 9; |
| 2.7 | 5' TTTCATCCCATCTGTATC | 3', SEQ ID NO.: 10; and |
| 2.8 | 5' TGTGCCCGTCCCGCGAAC | 3', SEQ ID NO.: 11 | are all synthesized and used as primers as sequencing progressed.

Example 4

Mapping of the ZRP2 transcription start point

The plasmid pZ2B is digested with SaII liberating an 8 kbp fragment. This fragment is digested again with PvuII. The resulting 401 bp fragment ligated into SaII/SmaI digested pBluescript (KS) resulting in pZ2.01. A $^{32}$P-labelled antisense RNA probe is synthesized from SaII finearized pZ2.01 template using $T_7$ RNA polymerase. The probe is gel purified on a 5% denaturing polyacrylamide gel, hybridized to 10 μg of root total RNA, and treated with RNase according to the ribonudease protection assay (Arabion). Markers and the protected ZRP2 mRNA are run on an 8% denaturing polyacrylamide gel and exposed to X-ray film at −80 C. for one day. Low molecular weight RNA markers are purchased from Gibco BRL and end-labeled with $^{32}$P as described from the manufacturer. The 102 and 81 bp markers are $^{32}$P-labeled and synthesized with $T_7$ polymerase from XhoI and HindIII finearized pBluescript (KS).

Example 5

In vitro Transcription Assays

Maize seeds are germinated under a 12 h fight/dark cycle for 3 or 5 days from which root and leaf nuclei are isolated respectively. Roots cut into 4–10 mm pieces are immersed in ether for 4 min. Leaf tissue is harvested within 4–6 h of the onset of light to ensure maximal cab transcription. (Taylor (1989) Plant Cell 1:259–264.) The primary leaf is removed from the mesocotyl node and two grams of fresh leaves are used per isolation. All reagents and supplies are precooled to 4° C. The leaves are immersed in ether for 3 min. The ether is poured off the root segments and the leaves and 5 ml of extraction buffer (2.5% ficoll 400, 4.0% dextran T40, 250 mM sucrose, 25 mM Tris-HCL pH 7.8, and 10 mM MgCl) is added to the mortar containing the roots and leaves. The plant tissue is ground and the homogenate is filtered through two layers of 149 μm and 60 μm nylon mesh into a corex tube. To the filtrate is added 500 μl of 20% Triton-x-100. After mixing by inversion, the tubes are centrifuged for 2–3 min at 2,000 rpm in a HB-4 rotor. The supernatant is drained off, and the pellet is resuspended in 10 ml wash buffer (extraction buffer plus 0.1% Triton-x-100 v/v) and the centrifugation step is repeated. The supernatant is decanted and the pellet is resuspended in 300 μl extraction buffer and quick frozen in liquid $N_2$, and then stored at −80° C.

The in vitro run on transcription reaction includes 48 μl of premix (325 μM ATP, CTP, GTP and 50 mM $NH_2SO_4$), 12 μl RNASIN (Promega), 50 μl UTP$^{32}$ (500 μCi), and 290 μl of nuclei. The reaction is carded out for 30 min with occasional mixing, and RNA is isolated by centrifugation of the reaction to pellet the nuclei. The supernatant is removed and the pellet is resuspended in 30 μl sterile $H_2O$. Five unit of DNASE (Promega) are added and the mixture is allowed to incubate for 10 min at room temperature. The volume is brought up to 370 μl with elution buffer (20 mM Tris-HCl, 1 mM EDTA, 0.5% SDS, 5 μg/ml yeast RNA). The mixture is extracted with phenol/chloroform (1/1) two or three times and then passed over a Bio-gel P60 column. The average cpm is determined by counting three, 2 μl aliquots with scintillation spectroscopy.

In vitro run on transcription assays reveal that the ZRP2 gene is transcribed at a high level in roots, while ZRP2 transcription is not detectable in leaves.

Example 6

Construction of plasmids

Figure 6:
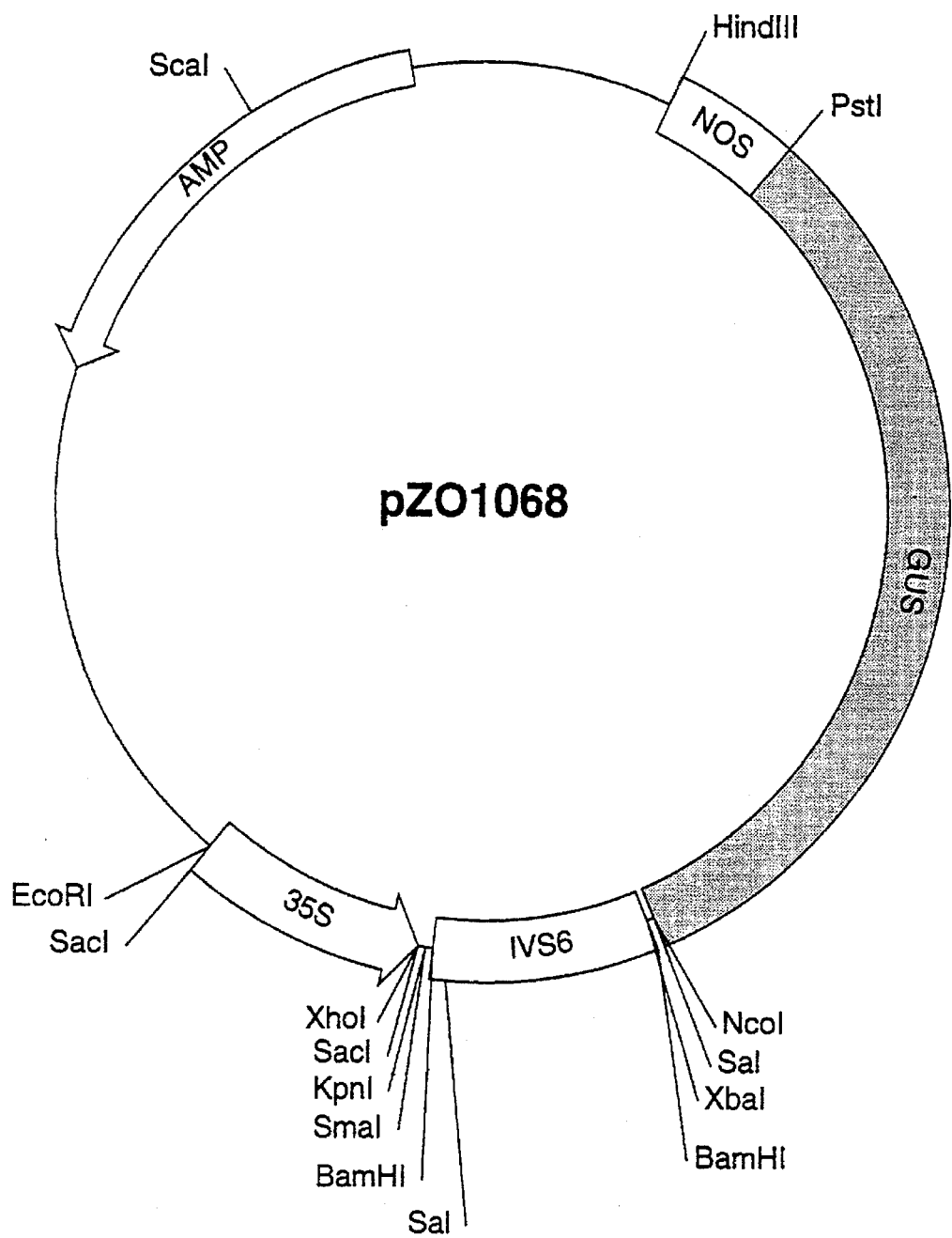
FIG. 6 describes the transformation vector pZO1068 which is a pUC18-based monocot expression vector which has a 35S promoter, an Adh 6 intron, a polylinker containing an XbaI site at the 5' end of GUS and a NOS terminator.
Figure 7:
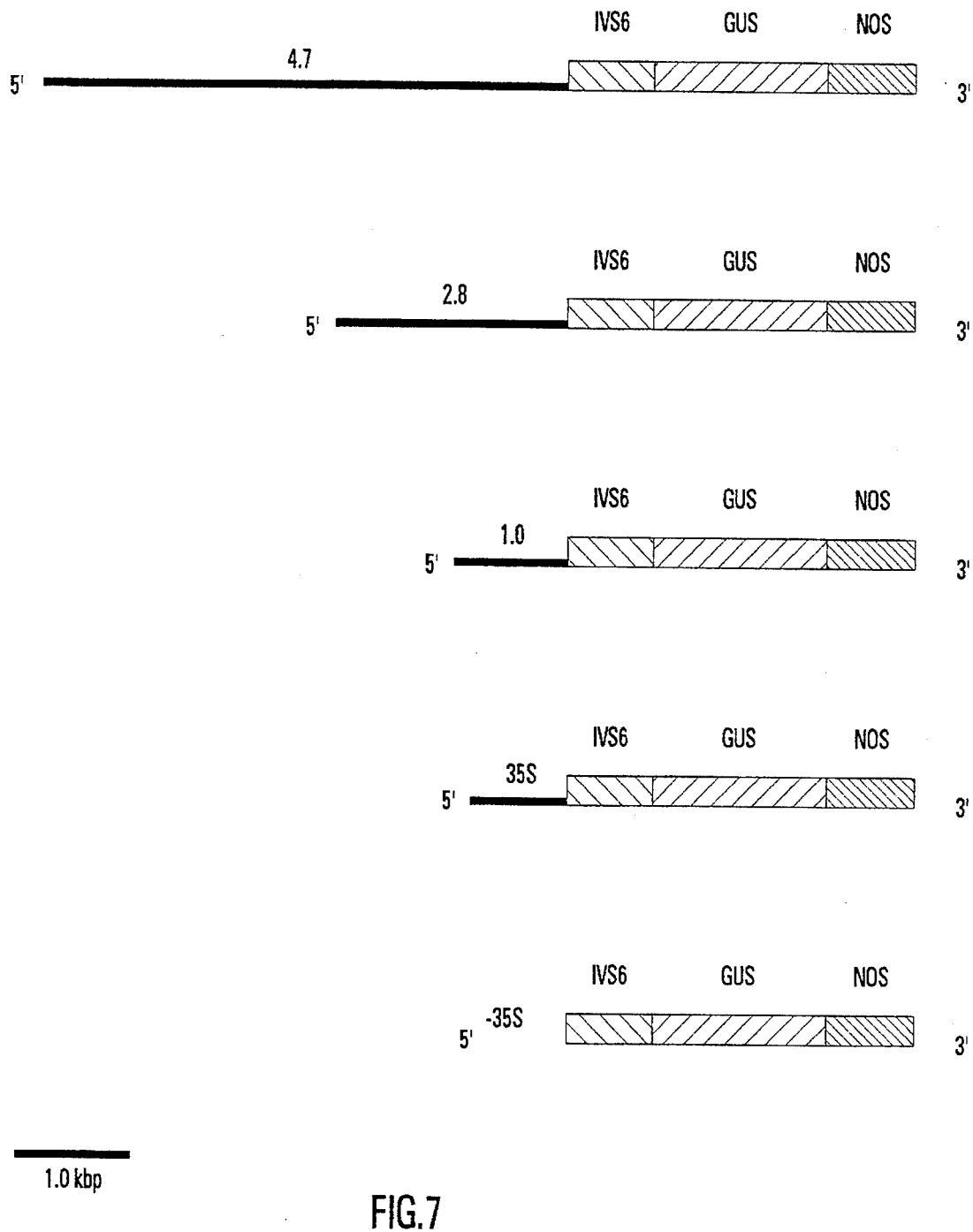
FIG. 7 describes a schematic of ZRP2 promoter elements and 35S/GUS fusion constructs used in transient-expression assays. The ZRP2 promoter elements include: ZRP2; a 2.0 kbp fragment, ZRP2(2.0); and a 1.0 kbp fragment, ZRP2 (1.0).
Figure 9:
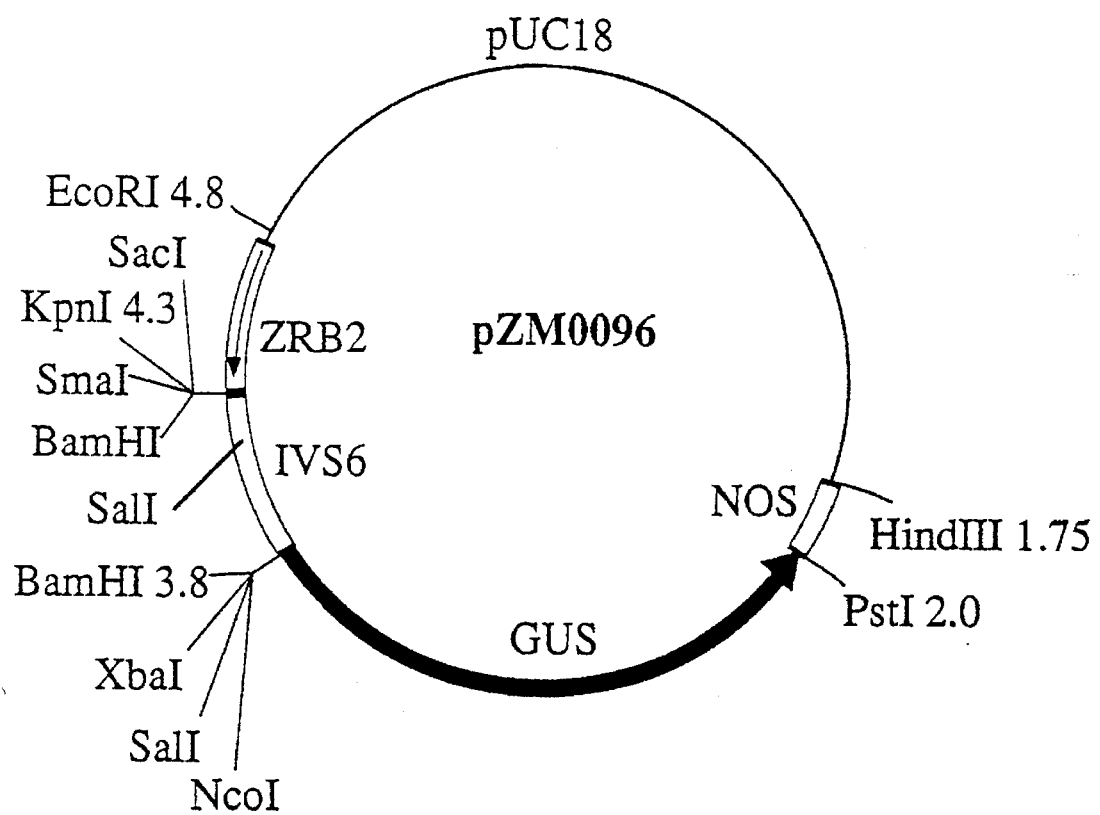
FIG. 9 describes the transformation vector pZM0096 used in corn tissue transformation studies which includes the ZRP2 promoter, the 4.7 kbp region of the genomic ZRP2 DNA clone.

Five different promoter/GUS transcriptional fusion constructs are used in the transient expression assays: 1) pZO1068; 2) pZO-35S1068 3)pZ2.47SATG in pZO1068; 4) pZ2.2HATG in pBluescript (SK); and 5) pZ2.1EATG in pZO1068, (FIG. 7). Plasmid pZO1068 depicted in FIG. 6 contains a 35S/INV6/GUS/NOS transcription fusion. The construct pZ2.47SATG in pZO1068 is used in Example 8 in transformation studies with maize; this plasmid is also designated PZM0096 (FIG. 9). The promotedess construct is constructed by digesting out the 35S promoter with SacI and religating the plasmid to form pZO-35S1068. Plasmids pZ2.47SATG and pZ2.1EATG in pZO1068 are made as follows: The 4.5 kbp SalI fragment from pZ2.45SS in pBluescript (KS) is cloned in the proper orientation into SalI digested pZ2.1ES in pBluescript (KS) to form pZ2.47SS in pBluescript (KS) (pZ2.1ES in pBluescript (KS) and pZ2.45SS in pBluescript (KS) are described above in Example 3). A synthetic linker comprised of the following oligonucleotides:

1) 5' CATACAAGAGCAACAAGATACTGGCGCA-GAGGAGCAC 3' SEQ ID No: 12 and 2) 3' GTACGTATGTFCTCGTTGTTCTATGAC-CGCGTCTCCTCGTGAGCT 5', SEQ ID No:13 is cloned into the SphI and XhoI sites of pZ2.1ES and pZ2.47SS in pBluescript (KS) to form pZ2.1EATG and pZ2.47SATG in pBluescript (KS). The oligonucleotide comprise base pair +26 through +61 of FIG. 1 (SEQ ID NO: 1). The XhoI/SacI fragments from pZ2.1EATG and pZ2.47SATG in pBluescript (KS) are cloned into pZO1068 that is sequentially digested with XhoI then SacI to form pZ2.1EATG and pZ2.47SATG in pZO1068. Plasmids pZ2.47SATG in pZO1068 and pZ2.1EATG in pZO1068 contain 4.7 kbp and 1.0 kbp of sequence that is upstream of the first putative ZRP2 translation start site. A ZRP2 promoter/GUS fusion containing 2.0 kbp of the 5' ZRP2 promoter region is constructed by digesting pZ2.47SATG in pZO1068 with HindIII. This fragment contains 2.0 kbp of ZRP2 promoter together with the IVS6/GUS/NOS cassette, and is cloned into HindIII digested pBluescript (SK) to form pZ2.2HATG in pBluescript (SK).

Example 7

Transient Expression

The roots and leaves used in the transient expression assay are similar to those used in the in vitro run-on transcription experiments. Petri dishes containing 1% water/agar covered with filter paper are prepared, and approximately 15–20 roots and four leaves are placed on each petri dish.

Each plate of roots are shot once with 5 µg of pZO1068 DNA, and the leaves are shot once with 1 µg of pZO1068 DNA. Equal molar amounts of the other construct are used. The procedures for microcarrier preparation and coating DNA onto microcarrier are well known in the art and the procedure as described by Sanford are followed in this example. (Sanford et al., (1993) Meth Enzymol 217:483–509). The tungsten particles coated with DNA are delivered with the helium-driven PDS-1000/He system. Conditions are M17 tungsten particles, 8 mm macrocarrier travel distance, 28 inches Hg chamber vacuum, 1100 psi of helium pressure and 6 cm target distance. After bombardment with microprojectives, the roots are incubated at 25° C. in the dark and the leaves are incubated at 25° C. in the light for approximately 20 h. The leaves or roots still on filter paper are transferred to new petri dishes and incubated in 5.0 ml of buffer (0.1M NaPO$_4$(pH 6.8), 0.5 mM K$_3$Fe(CN)$_6$ and K$_4$Fe(CN)$_6$, 0.01M EDTA, and 0.1% Triton-x-100) containing 0.5 mg/ml of the histochemical; substrate X-Gluronidase (X-Gluc, Clonetech). The tissue in X-Glue solution is incubated at 37° C. in the dark for 15–20 h. Blue spots are counted under a 10× stereo microscope. Counting blue spots is more convenient than measuring GUS activity because the root protein extracts displays background fluorescence (data not shown). In three independent root experiments the 35S promoter consistently displayed the highest activity and the promotedess construct (−35S) activity is negligible. The 1.0 kbp ZRP2 promoter fragment activity is significantly higher than the −35S control, but consistently lower than the 4.7 kbp fragment. The 4.7 kbp ZRP2 promoter appears to have the strongest activity of the ZRP2 promoter constructs. (FIG. 8).

Other experiments are performed testing the same promoter fragment constructs in leaves. The ZRP2 promoter fragments demonstrate GUS activity in leaves, however the distribution of the activity is primarily localized in the base of the leaves whereas 35S promoter activity appears throughout the entire leaf.

Example 8

Stable transformation of maize with ZRP2 promoter/GUS fragments

Corn ears, Hi II, 9 to 12 days after pollination are harvested for embryo isolation, sterilized and rinsed in sterile water. Embryos are excised from the kernels and transferred to bottles containing 500 mL of N6ap1D medium (Rhodes, Calif. et at., (1988) Biofrech. 6:56–60). The bottle is shaken vigorously for 2 seconds and the embryos separated from endosperm tissues by passage through a 1000 um screen. Ten to 50 embryos are transferred to a 5 cm filter paper disc. Excess media is removed by aspiration. The disc is transferred to a petri dish containing solid N6ap1D medium. The position of each embryo is adjusted and the embryos are stored in the dark at 27° C. for 1 hour to 5 days.

The filter paper discs, with embryos, are transferred to petri dishes containing solid N6ap1D medium supplemented with 0.5M mannitol. Within 10 hours of transfer the embryos are subjected to particle bombardment DNA delivery or "shot" with the Biolistic PDS-1000/He Particle Delivery System using a standard Sanford protocol except that the ethanol (100%) is added to the particles so that the final volume of the suspension is 900 µL.

The plasmid comprising the 4.7 kbp promoter region used in the transformation of maize tissue is described in FIG. 9 and corresponds to pZM0096.

Figure 10:
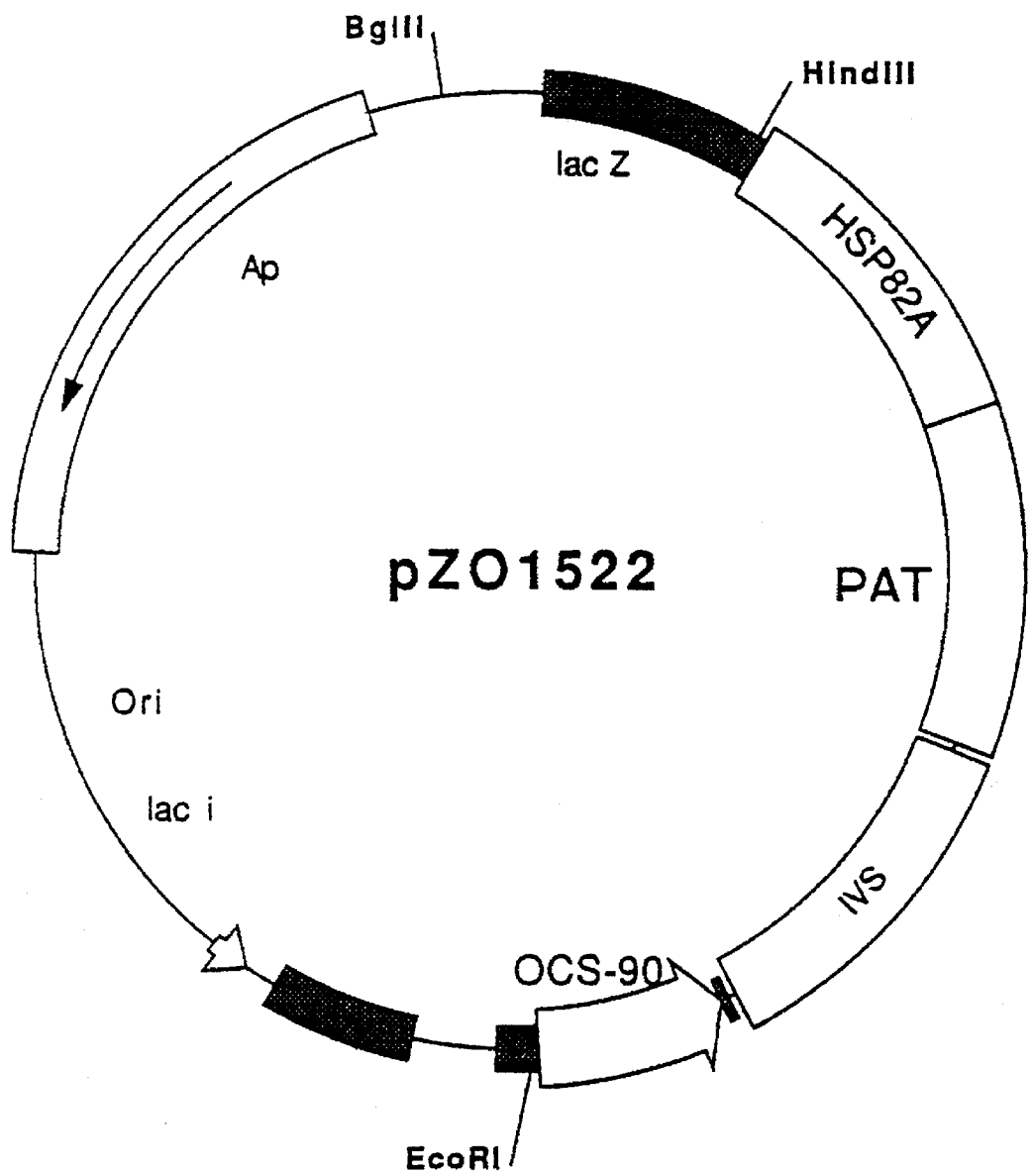
FIG. 10 describes the vector pZO1522 which is used in corn tissue transformation studies with the vector pZM0096 and encodes the PAT selectable marker gene.

The pZM0096 plasmid is delivered simultaneously with plasmid pZO1522 depicted in FIG. 10. pZO1522 encodes the Streptomyces hygroscopicus phosphinothricin acetyl-transferase (PAT) gene, the expression of which confers Basta resistance to transformed tissue. (Thompson C. J. et at., (1987) EMBO J. 6:2519–2523). Basta, common name glufosinate-ammonium, is a chemical herbicide containing phosphinothricin which inhibits glutamine synthase. The practice of co-shooting or mixing plasmid DNA's for particle delivery is known and described in the art (Gordon-Kamm et at., 1990, Plant Cell 2:603–681). The final volume of the suspension containing DNA-coated tungsten particles and ethanol is 900 µL, prior to delivery to the embryos.

Following particle delivery the embryos and filter paper discs are kept on N6ap1D medium supplemented with 0.5M mannitol for 6 to 18 hours then transferred to fresh N6ap1D medium without selective agents for 0 to 5 days. Finally, the embryos and filter paper supports are transferred to solid N61D medium supplemented with 12 to 24 mg/L of Basta.

Sixty days after transformation, callus and embryo tissue which continues to grow on N61D medium containing Basta are transferred to fresh medium containing 24 mg/L Basta. Samples of at least 50 µg of these transformant tissues are removed and analyzed for the presence of the DNA originally delivered by particle bombardment using PCR techniques.

To regenerate plants, the callus is transferred to petri dishes containing solid MSap medium without growth hormones and stored in the dark at 27° C. for 15 days. Plant shoots formed under these conditions are transferred to fresh medium in boxes and stored at 27° C. under a cycle of 18 hours/24 hours of bright light. Ten days after transfer to boxes the developing plants that are greater than 3 inches in height and possess a root system are transferred to soil and stored in a growth chamber for 48 hours total. The relative humidity is adjusted to 50% and the plants maintained in a growth chamber for 1 to 2 weeks then transplanted into 5 gallon pots and maintained in a greenhouse with under a cycle of 18 hours/24 hours of bright light.

---

It is claimed:

1. An isolated DNA fragment comprising, the nucleotide sequence located at positions 1633 to 2633 of SEQ ID No. 1 or a nucleotide sequence having 85% sequence identity to positions 1633 to 2633 of SEQ ID No. 1, the complement of which hybridizes under stringent hybridizing conditions to said positions, and wherein said isolated DNA fragment controls transcription preferentially in plant roots.

2. An isolated DNA fragment according to claim 1, wherein the fragment is the nucleotide sequence located at positions 1633 to 2633 of SEQ ID No. 1.

3. An isolated DNA fragment according to claim 1, further comprising the nucleotide sequence located at positions 633 to 2633 of SEQ ID No. 1 or a nucleotide sequence having 85% sequence identity to positions 633 to 2633 of SEQ ID No. 1, the complement of which hybridizes under stringent hybridizing conditions to said positions.

4. An isolated DNA fragment according to claim 1, further comprising the nucleotide sequence located at positions 1 to 2633 of SEQ ID No. 1 or a nucleotide sequence having 85% sequence identity to positions 1 to 2633 of SEQ ID No. 1, the complement of which hybridizes under stringent hybridizing conditions to said positions.

5. An isolated DNA fragment according to claim 4, wherein the fragment is the nucleotide sequence located at positions 1 to 2633 of SEQ ID No. 1.

6. A recombinant DNA molecule comprising the fragment according to claim 1, operably linked to a heterologous coding sequence.

7. A recombinant DNA molecule comprising the fragment according to claim 3, operably linked to a heterologous coding sequence.

8. A recombinant DNA molecule comprising the fragment according to claim 4, operably linked to a heterologous coding sequence.

9. A recombinant DNA molecule according to claim 6 or 7, wherein said heterologous coding sequence is selected from the group consisting of insecticidal coding sequences, herbicidal resistance coding sequences, anti-microbial coding sequences, anti-fungal coding sequences, anti-vital coding sequences, nutritional quality coding sequences and anti-feedant coding sequences.

10. A recombinant DNA molecule according to claim 8, wherein said heterologous coding sequence is selected from the group consisting of insecticidal coding sequences, herbicidal resistance coding sequences, anti-microbial coding sequences, anti-fungal coding sequences, anti-vital coding sequences, nutritional quality coding sequences and anti-feedant coding sequences.

11. A plant transformation vector comprising the recombinant DNA molecule according to claim 8.

12. A plant transformation vector according to claim 11, wherein the vector is a plasmid.

13. A plant cell, tissue or protoplast transformed with a DNA molecule according to claim 8.

14. A plant cell, tissue or protoplast according to claim 13, wherein said transformed cell, tissue or protoplast is from a corn plant.

15. A method of preferentially expressing a heterologous coding sequence in plant roots under transcriptional control of a promoter according to claim 1 comprising
 a) transforming plant cells, tissue or protoplasts with a vector wherein said vector comprises the promoter operably linked to a heterologous coding sequence,
 b) growing the transformed cells, tissue or protoplasts comprising the vector, and
 c) producing plants from said transformed cells, tissue or protoplasts
wherein the heterologous coding sequence is preferentially expressed in plant roots under control of said promoter.

16. A method according to claim 15, wherein the transformed plant cells, tissue or protoplasts are from maize.

17. A method according to claim 15, wherein said heterologous coding sequence is selected from the group consisting of insecticidal coding sequences, herbicidal resistance coding sequences, anti-microbial coding sequences, anti-fungal coding sequences, anti-viral coding sequences, nutritional quality coding sequences and anti-feedant coding sequences.

18. Plants produced according to the method of claim 15.

19. Plants according to claim 18 wherein said plants are maize.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 2636 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
GGGCCCAAAG GAAGGAAGTA CTTCAGTGGA TCAAGATGTT GATGTTCCCT GATGGGTATG      60
CAGCTAACCT GAGTAGGTGG GGTGAACTTA TCTACTCTGT GAGTCTTAGG GATGAAGAGT     120
CATGACTTCC ACATATGGAT TGAACAGATT CTTCTCTGTG CATGGACAAT CTGGGCGGC      180
ATCCAACAAC CCTCATGGAT CGCCCGGCCA ATCGCCGCAC CAGTCCATCC GCCCACCTCG     240
ATGAGACTTA TGTTCTTAGT GTTGAGACTT CAGAACTTAT TGATAATGCT GTATTGGATA     300
CTTATGTTTG TGTTCGATAC TTATGTGAGA ACTTGAGACT TATGAGACTT ATGTTCTTGA     360
TACTTATGTT TGTGTTGAGA ACTTGGATAT TTATGTTTGT GTTGGATACT TATGTCTGTG     420
ATGATATATG TGATGTATAT ATGTGATGTA TATGTGACAT ATGTGATGTA TATGTGGTAT     480
CTTTTGTTTG TTTGGATGGA ATAGAGAAAG CAAATAAAAA TGTGTATACT GGTCACTTTG     540
TCGAGTGTAA CACTCGGCAA AAAGGTGCTT TGCCGAGTGT TAGGGCCATA GCACTCGGTA     600
GAGAACCAAT ACTTAGGCAC CGGTAAAGCT TTTTGGCGA GTGTTGTGGC CCTGGCACTC      660
AGCTTTGCCG AGTGCCTCAC AGAGCACTCG ACAAAGAACC TGACAAATGG ACCCGCTGGT     720
AAATCCTTTA CCGAGTGCAG GTCAGTAGAC ACTCGGCAAA GGTAACTTCT TTGCCGAGTG     780
CCGCTTAGAA CATTTGACAA AGGGTCATCT CCGTTACCCG GTGTCGTGAC GGCCGCTTTT     840
CTTTGCCGAG TGCCTGATAG AAAGTACTCG GCAAGAAGT CGTTGCCAAT GTATTGTTCG      900
CTGAGGTCTC TTTGTCAAGT ATTACACTCG GCAAAGACTG TGCCGAGTGT TTTTCAGACT     960
TTGCCGAGTG GTTTAAGCAC TCAGCAAAGC GCTCGATTTC GGTAGTGACG GTTGTTTGGC    1020
AATAGTAAAA TCCAGCCCTC TCCCGTGGGG AAAAAACTGG TAGGATCTGG CTCGTGGCTA    1080
AGATTCTCTT TCTTCCCTTT GTAAAAAAG AGAAGAAAAA AAAAACGACT GTCACGGTGC     1140
CTTGTCTGGT AATGATCGCG CGGTCGGCTC TGTCCTAACC CGTAAGATGG ACGGGAGCTG    1200
ATGATAGCGT GACCTCCAAA TAAACAACAA GGGCGTGTTC CCCGCGGTCG AATATTTAA     1260
GGGCCACTGA TTAGGTGCGG TTGAATACAT CAACTTCACG AACATCATCT GATCTGATCT    1320
GATTGGTCT GATATGATCT GGGTAGTCAT TTCTGCAATG AGCATCTATC AGGTGAACCA     1380
ATTAATATTG ATGACATTAT GAGTTCGAAG ATATACTCTA AAGTGTTATC TAAATACAGA    1440
AGACATTCGT TCGTTCTTTG CCTATAACTC TAAAAGGCTT GTAACACCCT CATTCATCCT    1500
CTATATACGA AGACTCTCTC CTATCATTTT TATCGATTTA TTTTTTTTAT ATTTAGACAA    1560
TGGAATTAAA TAGAACTAAA ATATATATAA GATGATATCT GAGGACCCGA GATGGTAATG    1620
GGGACTCGAT CCTCGATTCT CCACGGAGAA TTCCTCTAGG ATATAGGTAA TTTGTCCCCA    1680
```

```
CGAGGATTGA  AACGGGGTAA  TTTGGTCCCC  ATGTGCCCGT  CCCGCGAACT  TCTCTTGATC  1740

TAAATTAGTC  TATTTCCATG  TTAAAACTAT  ACTAAAAATT  TAATACACAG  TCTATTATAA  1800

AATAGCAAAC  TAAATTCTAA  AGTTGATGCA  TCTTGTAATT  TTAAATCTGG  TTTGTTCAAG  1860

TTATATTCAT  TTGATATAAT  AAATTTGAAT  TTGACTCTTA  ATATCGTATT  TTTTCCTAAC  1920

GGGGACGGAT  TCTCCACGGG  GATAAATTCC  ATGATACAGA  TGGGATGAAA  GAAAAATCTC  1980

CCGTATGAAC  TTTTGCAGGA  ATGGGGATGG  GCCAGAGAAA  TTTTCTCCCT  GCGGGGACGG  2040

GGGAGCCATA  TCCTCGGTGG  AGAATTTCCC  ATTATCATCC  TTATTTGTGG  TACATATATA  2100

TGCATAATCT  TTTTTTTTTG  ACTGACATGT  GGGAAAGTAT  CCCATCTCAA  TAGTAGAAAA  2160

TCTTGGGAAC  GGTAGGATCG  AACACAAAGA  TCAGCTAGCT  TGTAATCACC  GAGCCATATA  2220

GCTAGAGGGT  AATAGATCAT  GAATCAAATG  TTTTTTTCAT  AAATTATTAA  GGCTCTAAAT  2280

TATTTTTAAT  TTAAAAATAA  ATAAAAATAT  AGTTCGATTC  TTACATTTTA  TAGTGTAAAA  2340

CTTTAAAGTC  TATTATTACC  CCTACTTATT  GAGTTATGGT  TCAGTTCTTG  TCGACGGAGA  2400

GTAATGAGAT  ATAGAATAAG  GTACCCTATA  GAATAAAGAA  TCTTTCTCTG  AAAAGTCTGA  2460

CGTACGTAAA  TAAGATATAA  TAAAAAAAAT  ACAAAGAGAA  GCGCTGGACT  GGAGATGCTC  2520

CTATATGCGG  CAATGCCTGT  GCTTATAAAT  AGCCACCTCG  GTCGGCAAGG  ACATGAACGG  2580

CGGACGCAGT  GTGCATGCAT  ACAAGAGCAA  CAAGATACTG  GCGCAGAGGA  GCAATG      2636
```

( 2 ) INFORMATION FOR SEQ ID NO:2:

( i ) SEQUENCE CHARACTERISTICS:
        ( A ) LENGTH: 2329 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..1850
        ( D ) OTHER INFORMATION: /codon_start= 51

( x i ) SEQUENCE DESCRIPTION: SEQ ID NO:2:

```
CGCAGTGTGC  ATGCATACAA  GAGCAACAAG  ATACTGGCCG  CAGAGGAGCA  ATG CCC                         56
                                                             Met Pro
                                                              1

GGC  ATG  GAT  GCC  TTC  GCT  GCT  GTG  TCA  CTA  CTC  GCC  ACA  CTC  TTT  CTG           104
Gly  Met  Asp  Ala  Phe  Ala  Ala  Val  Ser  Leu  Leu  Ala  Thr  Leu  Phe  Leu
          5                        10                      15

GTT  CGT  GCG  GCA  GCT  GCC  CAT  CCT  CCG  GCG  GCG  GCT  GCG  GAC  GAC  ATG           152
Val  Arg  Ala  Ala  Ala  Ala  His  Pro  Pro  Ala  Ala  Ala  Ala  Asp  Asp  Met
     20                       25                      30

ACG  CCG  ACG  GAC  TAT  TGG  CGA  GCG  GTG  CTT  CCT  GAG  ACC  CCG  ATG  CCC           200
Thr  Pro  Thr  Asp  Tyr  Trp  Arg  Ala  Val  Leu  Pro  Glu  Thr  Pro  Met  Pro
 35                 40                      45                          50

CGA  GCC  ATA  CTC  GAC  CTA  TTG  ACC  ACA  TCT  ACA  GGT  GAG  GAA  GGC  TCA           248
Arg  Ala  Ile  Leu  Asp  Leu  Leu  Thr  Thr  Ser  Thr  Gly  Glu  Glu  Gly  Ser
                    55                      60                      65

AGG  AAG  GTC  ACC  ACG  TCA  AAT  GGG  TAC  CAA  GGC  CAT  GAC  TTA  AGG  ACG           296
Arg  Lys  Val  Thr  Thr  Ser  Asn  Gly  Tyr  Gln  Gly  His  Asp  Leu  Arg  Thr
               70                      75                      80

GTC  AGC  ACA  TCA  TAT  GCA  TCT  CAA  GAT  GGG  GAC  AAC  TCA  TGG  AAG  GCC           344
Val  Ser  Thr  Ser  Tyr  Ala  Ser  Gln  Asp  Gly  Asp  Asn  Ser  Trp  Lys  Ala
          85                      90                      95

ACC  ATG  TCA  TAT  GGG  TTC  CAA  AGT  GGT  GAG  GGC  TCG  AGG  AAG  GTC  ACC           392
Thr  Met  Ser  Tyr  Gly  Phe  Gln  Ser  Gly  Glu  Gly  Ser  Arg  Lys  Val  Thr
```

|  |  |  |  |  |  |  |  |  |  |  |  |  |  |  |  |
|---|---|---|---|---|---|---|---|---|---|---|---|---|---|---|---|
| ACA | TCA | TAT | CCG | TAC | CGA | GGC | CAG | GAC | TTA | AGG | ATG | GTC | AGC | ACA | TCA | 440
| Thr | Ser | Tyr | Pro | Tyr | Arg | Gly | Gln | Asp | Leu | Arg | Met | Val | Ser | Thr | Ser |
| 115 |  |  |  | 120 |  |  |  |  | 125 |  |  |  |  | 130 |  |

```
                100                               105                              110

ACA TCA TAT CCG TAC CGA GGC CAG GAC TTA AGG ATG GTC AGC ACA TCA                440
Thr Ser Tyr Pro Tyr Arg Gly Gln Asp Leu Arg Met Val Ser Thr Ser
115                 120                 125                 130

TAT GTA TCT CAA GAT GAG GAC AAC TCA TGG AAG GTC TCG ATG CCA TCT                488
Tyr Val Ser Gln Asp Glu Asp Asn Ser Trp Lys Val Ser Met Pro Ser
                    135                 140                 145

AGG TTC CAA GTT GGT GAG GGC TTA AGG AAG CTC ACC ACA CCA TTC GAA                536
Arg Phe Gln Val Gly Glu Gly Leu Arg Lys Leu Thr Thr Pro Phe Glu
            150                 155                 160

TCA CAA AGG AAG GAC TCA AGG AAG GCC ACC GCA TCA TAT GGA ATC CAA                584
Ser Gln Arg Lys Asp Ser Arg Lys Ala Thr Ala Ser Tyr Gly Ile Gln
        165                 170                 175

GAT GAT GAG GAC ACA AGG AAG GCC ACT ACA TCA TAT GGA ATC CAT GGG                632
Asp Asp Glu Asp Thr Arg Lys Ala Thr Thr Ser Tyr Gly Ile His Gly
    180                 185                 190

GAG GAC CCA AGA AAG GCC ACC ACG TCA TAT GGT TCC CAG GAT GAG AAG                680
Glu Asp Pro Arg Lys Ala Thr Thr Ser Tyr Gly Ser Gln Asp Glu Lys
195                 200                 205                 210

GGA TCA AGG AAG GTC ATA ATG TCA TAT GGG TCT AAT GGT GAG GAT GAT                728
Gly Ser Arg Lys Val Ile Met Ser Tyr Gly Ser Asn Gly Glu Asp Asp
                215                 220                 225

CCA AGA AAG GCC ACC ACA TCA TAT GGA ATA CAA GAT AAA GAG TAT CCC                776
Pro Arg Lys Ala Thr Thr Ser Tyr Gly Ile Gln Asp Lys Glu Tyr Pro
            230                 235                 240

AGG AAG GCC ACC ACA TCT TAT GGA GTT CAA GGT GAG AAG GAC CCA AGG                824
Arg Lys Ala Thr Thr Ser Tyr Gly Val Gln Gly Glu Lys Asp Pro Arg
        245                 250                 255

GAA GCT ACC ATC TCA TAT GGG TCC CAG GAT GAT GAG GAT TCT AGA AAA                872
Glu Ala Thr Ile Ser Tyr Gly Ser Gln Asp Asp Glu Asp Ser Arg Lys
    260                 265                 270

GTC AAC ATG TCA TAT GGG TCT AAT GGT GAG GAC GAC CCA AGA AAG GCC                920
Val Asn Met Ser Tyr Gly Ser Asn Gly Glu Asp Asp Pro Arg Lys Ala
275                 280                 285                 290

ACC ACA TCA TAT GGG TCC CAT GGT GAG TAT GAA TCA AAT AAG GCC ACA                968
Thr Thr Ser Tyr Gly Ser His Gly Glu Tyr Glu Ser Asn Lys Ala Thr
                295                 300                 305

ATG TCA TAT GGG TTC CAA GGC ATG GAA GAT TTA AGG AAG GCC ACC ACA               1016
Met Ser Tyr Gly Phe Gln Gly Met Glu Asp Leu Arg Lys Ala Thr Thr
            310                 315                 320

TCA TAT GGA ATA CAA GAT GAA GAG TAT CCA AGG AAG GCC ACC ACA TCA               1064
Ser Tyr Gly Ile Gln Asp Glu Glu Tyr Pro Arg Lys Ala Thr Thr Ser
        325                 330                 335

TAT GGA GTT CAA GGT GAG GAG GAC CCA AAG AAA GAT ACC ATG TCA TAT               1112
Tyr Gly Val Gln Gly Glu Glu Asp Pro Lys Lys Asp Thr Met Ser Tyr
    340                 345                 350

GGG TCA CAA GAT GAC GAG GAA TCT AGA AAA ATC AGC ATC TCA TAT GGG               1160
Gly Ser Gln Asp Asp Glu Glu Ser Arg Lys Ile Ser Ile Ser Tyr Gly
355                 360                 365                 370

TCT AAT GGT GAG AAC GAC TCA AGA ACG TCC ACC ACA TCA TAT GGG TCC               1208
Ser Asn Gly Glu Asn Asp Ser Arg Thr Ser Thr Thr Ser Tyr Gly Ser
                375                 380                 385

CAA GGT AAG GAG ATC CTA AGA AAG GTC ACC ACG TCA TGT GAT AGG TAC               1256
Gln Gly Lys Glu Ile Leu Arg Lys Val Thr Thr Ser Cys Asp Arg Tyr
            390                 395                 400

CAC AGT TGT GAA GAT GAT GCG CGG AAG GCC ACC GCA TCA CAT AGA GCT               1304
His Ser Cys Glu Asp Asp Ala Arg Lys Ala Thr Ala Ser His Arg Ala
        405                 410                 415

GAA GGT AAG CAG GAC ATG AAG AAG ATC AGC ATA TCA TAT GGA TCT CAT               1352
Glu Gly Lys Gln Asp Met Lys Lys Ile Ser Ile Ser Tyr Gly Ser His
```

-continued

|  |  |  | 420 |  |  |  |  | 425 |  |  |  |  | 430 |  |  |  |
|---|---|---|---|---|---|---|---|---|---|---|---|---|---|---|---|---|
| CGA | AGT | GGG | GAG | CAC | TCA | TTG | AGA | ACC | ACC | AGT | ACA | AGA | GAG | AAA | GGT | 1400 |
| Arg | Ser | Gly | Glu | His | Ser | Leu | Arg | Thr | Thr | Ser | Thr | Arg | Glu | Lys | Gly |  |
| 435 |  |  |  |  | 440 |  |  |  |  | 445 |  |  |  |  | 450 |  |

| GAC | ACA | AGT | AAA | GGG | GAC | ATC | CAT | CAC | CAT | GAC | CAT | GCT | GCC | GTT | CAC | 1448 |
|---|---|---|---|---|---|---|---|---|---|---|---|---|---|---|---|---|
| Asp | Thr | Ser | Lys | Gly | Asp | Ile | His | His | His | Asp | His | Ala | Ala | Val | His |  |
|  |  |  |  | 455 |  |  |  |  | 460 |  |  |  |  | 465 |  |  |

| ATC | CAC | AGC | AGC | GGC | AAC | AAG | CTA | GTA | GCA | GAT | GTT | TTC | TTC | TTC | CAC | 1496 |
|---|---|---|---|---|---|---|---|---|---|---|---|---|---|---|---|---|
| Ile | His | Ser | Ser | Gly | Asn | Lys | Leu | Val | Ala | Asp | Val | Phe | Phe | Phe | His |  |
|  |  | 470 |  |  |  |  | 475 |  |  |  |  | 480 |  |  |  |  |

| GAC | GTC | CCT | ACG | ACC | AGG | GTC | CGT | AAT | CAC | GCC | GAT | CAT | CCC | ACC | GAC | 1544 |
|---|---|---|---|---|---|---|---|---|---|---|---|---|---|---|---|---|
| Asp | Val | Pro | Thr | Thr | Arg | Val | Arg | Asn | His | Ala | Asp | His | Pro | Thr | Asp |  |
|  |  | 485 |  |  |  |  | 490 |  |  |  |  | 495 |  |  |  |  |

| CAC | CAC | CCT | ACC | ACC | TCT | GCT | GCC | TCT | CCG | CGA | GGC | CGA | CGC | GCT | CCC | 1592 |
|---|---|---|---|---|---|---|---|---|---|---|---|---|---|---|---|---|
| His | His | Pro | Thr | Thr | Ser | Ala | Ala | Ser | Pro | Arg | Gly | Arg | Arg | Ala | Pro |  |
|  | 500 |  |  |  |  | 505 |  |  |  |  | 510 |  |  |  |  |  |

| GTT | CTC | CAC | CGG | GCG | CTT | CGC | CGA | CAT | CCT | CGC | CAT | GTT | CGC | GCC | GAC | 1640 |
|---|---|---|---|---|---|---|---|---|---|---|---|---|---|---|---|---|
| Val | Leu | His | Arg | Ala | Leu | Arg | Arg | His | Pro | Arg | His | Val | Arg | Ala | Asp |  |
| 515 |  |  |  |  | 520 |  |  |  |  | 525 |  |  |  |  | 530 |  |

| GAC | ATC | CGA | CGC | CAT | GGG | CGA | AGA | GAT | ACG | GTC | GAC | GCT | CGA | CAC | CTG | 1688 |
|---|---|---|---|---|---|---|---|---|---|---|---|---|---|---|---|---|
| Asp | Ile | Arg | Arg | His | Gly | Arg | Arg | Asp | Thr | Val | Asp | Ala | Arg | His | Leu |  |
|  |  |  |  | 535 |  |  |  |  | 540 |  |  |  |  | 545 |  |  |

| CGA | GAA | CAC | GCG | CCC | GCT | CCC | CGG | CGA | GAA | GGC | CGA | CTG | CGA | CAC | CTC | 1736 |
|---|---|---|---|---|---|---|---|---|---|---|---|---|---|---|---|---|
| Arg | Glu | His | Ala | Pro | Ala | Pro | Arg | Arg | Glu | Gly | Arg | Leu | Arg | His | Leu |  |
|  |  |  | 550 |  |  |  |  | 555 |  |  |  |  | 560 |  |  |  |

| CCT | CGA | GTC | TCT | CGC | CAG | GAT | ACC | CGC | CGT | CCT | CCT | CGG | GAC | ACG | CAA | 1784 |
|---|---|---|---|---|---|---|---|---|---|---|---|---|---|---|---|---|
| Pro | Arg | Val | Ser | Arg | Gln | Asp | Thr | Arg | Arg | Pro | Pro | Arg | Asp | Thr | Gln |  |
|  |  | 565 |  |  |  |  | 570 |  |  |  |  | 575 |  |  |  |  |

| CGT | CCG | CGC | TTT | CTC | CGG | CGA | CAT | GCC | CAC | CGA | TCC | TGC | CGG | CAC | GTC | 1832 |
|---|---|---|---|---|---|---|---|---|---|---|---|---|---|---|---|---|
| Arg | Pro | Arg | Phe | Leu | Arg | Arg | His | Ala | His | Arg | Ser | Cys | Arg | His | Val |  |
|  | 580 |  |  |  |  | 585 |  |  |  |  | 590 |  |  |  |  |  |

| GGC | GAA | GGG | GGG | GCG | GTA | TAACGTAACG | GCCGTGCAGA | AGCTCTCCGA | 1880 |
|---|---|---|---|---|---|---|---|---|---|
| Gly | Glu | Gly | Gly | Ala | Val |  |  |  |  |
| 595 |  |  |  |  | 600 |  |  |  |  |

| GTCACTGACG | GCGGCGGCGT | GCCATGACCT | GACGTACCAC | TACGACGTGT | TCTACTGCCA | 1940 |
|---|---|---|---|---|---|---|
| CACGACCAAC | CCGGCGGCCA | CGTACCTGGT | GAAGCTGGCA | GCCCAGGATG | GCGGGGCGGC | 2000 |
| GGACATGGAG | GCGTTGGTCG | TGTGCCACCT | CGACACGTCG | TTGTGGAGTC | CCAGACACCC | 2060 |
| ATTTTGGTG | GCGCACAGTC | TCAAGCCAGG | GGACGACGCA | GTCGTGTGTC | ATTTTCTCTC | 2120 |
| TAAGCTCAGC | ATCGTCTGGG | TCCCCGCTGG | CGAGCAGGGG | TGGCGTGCGT | GAAGTGAAGC | 2180 |
| CCAATTAGCG | TTAAGTACCC | GTGCTCAGAG | CTCTATCTGT | AACCTGTGTG | GACCTAACGT | 2240 |
| GGCTCTGTAA | TGCTAAATAA | AAACCTGCGT | CAATCATGTA | TCGTGATATT | TTATCTGTTT | 2300 |
| TAGCAAAAAA | AAAAAAAAA | AAAAAAAA |  |  |  | 2329 |

( 2 ) INFORMATION FOR SEQ ID NO:3:

( i ) SEQUENCE CHARACTERISTICS:
        ( A ) LENGTH: 600 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Pro | Gly | Met | Asp | Ala | Phe | Ala | Ala | Val | Ser | Leu | Leu | Ala | Thr | Leu |
|---|---|---|---|---|---|---|---|---|---|---|---|---|---|---|---|
| 1 |  |  |  | 5 |  |  |  |  | 10 |  |  |  |  | 15 |  |

| Phe | Leu | Val | Arg | Ala | Ala | Ala | Ala | His | Pro | Pro | Ala | Ala | Ala | Ala | Asp |
|---|---|---|---|---|---|---|---|---|---|---|---|---|---|---|---|
|  |  |  | 20 |  |  |  |  | 25 |  |  |  |  | 30 |  |  |

-continued

| | | | | | | | | | | | | | | |
|---|---|---|---|---|---|---|---|---|---|---|---|---|---|---|
| Asp | Met | Thr 35 | Pro | Thr | Asp | Tyr | Trp 40 | Arg | Ala | Val | Leu | Pro 45 | Glu | Thr | Pro |
| Met | Pro 50 | Arg | Ala | Ile | Leu 55 | Asp | Leu | Thr | Thr | Ser 60 | Thr | Gly | Glu | Glu |
| Gly 65 | Ser | Arg | Lys | Val 70 | Thr | Thr | Ser | Asn | Gly 75 | Tyr | Gln | Gly | His | Asp | Leu 80 |
| Arg | Thr | Val | Ser | Thr 85 | Ser | Tyr | Ala | Ser | Gln 90 | Asp | Gly | Asp | Asn | Ser 95 | Trp |
| Lys | Ala | Thr | Met 100 | Ser | Tyr | Gly | Phe | Gln 105 | Ser | Gly | Glu | Gly | Ser 110 | Arg | Lys |
| Val | Thr | Thr 115 | Ser | Tyr | Pro | Tyr | Arg 120 | Gly | Gln | Asp | Leu | Arg 125 | Met | Val | Ser |
| Thr | Ser 130 | Tyr | Val | Ser | Gln | Asp 135 | Glu | Asp | Asn | Ser | Trp 140 | Lys | Val | Ser | Met |
| Pro 145 | Ser | Arg | Phe | Gln | Val 150 | Gly | Glu | Gly | Leu | Arg 155 | Lys | Leu | Thr | Thr | Pro 160 |
| Phe | Glu | Ser | Gln | Arg 165 | Lys | Asp | Ser | Arg | Lys 170 | Ala | Thr | Ala | Ser | Tyr 175 | Gly |
| Ile | Gln | Asp | Asp 180 | Glu | Asp | Thr | Arg | Lys 185 | Ala | Thr | Thr | Ser | Tyr 190 | Gly | Ile |
| His | Gly | Glu 195 | Asp | Pro | Arg | Lys | Ala 200 | Thr | Thr | Ser | Tyr | Gly 205 | Ser | Gln | Asp |
| Glu | Lys 210 | Gly | Ser | Arg | Lys | Val 215 | Ile | Met | Ser | Tyr | Gly 220 | Ser | Asn | Gly | Glu |
| Asp 225 | Asp | Pro | Arg | Lys | Ala 230 | Thr | Thr | Ser | Tyr | Gly 235 | Ile | Gln | Asp | Lys | Glu 240 |
| Tyr | Pro | Arg | Lys | Ala 245 | Thr | Thr | Ser | Tyr | Gly 250 | Val | Gln | Gly | Glu | Lys 255 | Asp |
| Pro | Arg | Glu | Ala | Thr 260 | Ile | Ser | Tyr | Gly | Ser 265 | Gln | Asp | Asp | Glu | Asp 270 | Ser |
| Arg | Lys | Val 275 | Asn | Met | Ser | Tyr | Gly 280 | Ser | Asn | Gly | Glu | Asp 285 | Asp | Pro | Arg |
| Lys | Ala 290 | Thr | Thr | Ser | Tyr | Gly 295 | Ser | His | Gly | Glu | Tyr 300 | Glu | Ser | Asn | Lys |
| Ala 305 | Thr | Met | Ser | Tyr | Gly 310 | Phe | Gln | Gly | Met | Glu 315 | Asp | Leu | Arg | Lys | Ala 320 |
| Thr | Thr | Ser | Tyr | Gly 325 | Ile | Gln | Asp | Glu | Glu 330 | Tyr | Pro | Arg | Lys | Ala 335 | Thr |
| Thr | Ser | Tyr | Gly 340 | Val | Gln | Gly | Glu | Glu 345 | Asp | Pro | Lys | Lys | Asp 350 | Thr | Met |
| Ser | Tyr | Gly 355 | Ser | Gln | Asp | Asp | Glu 360 | Glu | Ser | Arg | Lys | Ile 365 | Ser | Ile | Ser |
| Tyr | Gly 370 | Ser | Asn | Gly | Glu | Asn 375 | Asp | Ser | Arg | Thr | Ser 380 | Thr | Thr | Ser | Tyr |
| Gly 385 | Ser | Gln | Gly | Lys | Glu 390 | Ile | Leu | Arg | Lys | Val 395 | Thr | Thr | Ser | Cys | Asp 400 |
| Arg | Tyr | His | Ser | Cys 405 | Glu | Asp | Asp | Ala | Arg 410 | Lys | Ala | Thr | Ala | Ser 415 | His |
| Arg | Ala | Glu | Gly 420 | Lys | Gln | Asp | Met | Lys 425 | Lys | Ile | Ser | Ile | Ser 430 | Tyr | Gly |
| Ser | His | Arg 435 | Ser | Gly | Glu | His | Ser 440 | Leu | Arg | Thr | Thr | Ser 445 | Thr | Arg | Glu |
| Lys | Gly 450 | Asp | Thr | Ser | Lys | Gly 455 | Asp | Ile | His | His | His 460 | Asp | His | Ala | Ala |

```
Val  His  Ile  His  Ser  Ser  Gly  Asn  Lys  Leu  Val  Ala  Asp  Val  Phe  Phe
465                 470                      475                      480

Phe  His  Asp  Val  Pro  Thr  Thr  Arg  Val  Arg  Asn  His  Ala  Asp  His  Pro
                485                      490                      495

Thr  Asp  His  His  Pro  Thr  Thr  Ser  Ala  Ala  Ser  Pro  Arg  Gly  Arg  Arg
               500                      505                      510

Ala  Pro  Val  Leu  His  Arg  Ala  Leu  Arg  Arg  His  Pro  Arg  His  Val  Arg
          515                      520                      525

Ala  Asp  Asp  Ile  Arg  Arg  His  Gly  Arg  Arg  Asp  Thr  Val  Asp  Ala  Arg
     530                      535                      540

His  Leu  Arg  Glu  His  Ala  Pro  Ala  Pro  Arg  Arg  Glu  Gly  Arg  Leu  Arg
545                 550                      555                      560

His  Leu  Pro  Arg  Val  Ser  Arg  Gln  Asp  Thr  Arg  Arg  Pro  Pro  Arg  Asp
                565                      570                      575

Thr  Gln  Arg  Pro  Arg  Phe  Leu  Arg  Arg  His  Ala  His  Arg  Ser  Cys  Arg
               580                      585                      590

His  Val  Gly  Glu  Gly  Gly  Ala  Val
               595                 600
```

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGCTTCTAGA TGCATGTCGA CGATATCGCA TGCTGCAGG           39

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GATCCCTGCA GCATGCGATA TCGTCGACAT GCATCTAGA           39

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CACAGCAGCG AAGGCATC           18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AAATAAGGAT GATAATGG           18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGTTATATTC ATTTGATA                                                                 18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCGAGCCATA TAGCTAGA                                                                 18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTTCATCCCA TCTGTATC                                                                 18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TGTGCCCGTC CCGCGAAC                                                                 18

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CATACAAGAG CAACAAGATA CTGGCGCAGA GGAGCAC                   37

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TCGAGTGCTC CTCTGCGCCA GTATCTTGTT GCTCTTGTAT GCATG           45